United States Patent
Alford, Jr. et al.

(10) Patent No.: US 8,575,206 B2
(45) Date of Patent: Nov. 5, 2013

(54) 2-SUBSTITUTED BENZIMIDAZOLES AS SELECTIVE ANDROGEN RECEPTOR MODULATORS (SARMS)

(75) Inventors: Vernon C. Alford, Jr., Spring House, PA (US); James C. Lanter, Exton, PA (US); Raymond A. Ng, Alpharetta, GA (US)

(73) Assignee: Janssen Pharmaceutica, NV (BE)

( * ) Notice: Subject to any disclaimer, the term of this patent is extended or adjusted under 35 U.S.C. 154(b) by 135 days.

(21) Appl. No.: 13/050,578

(22) Filed: Mar. 17, 2011

(65) Prior Publication Data

US 2011/0166102 A1  Jul. 7, 2011

Related U.S. Application Data

(62) Division of application No. 11/626,030, filed as application No. PCT/EP2007/060883 on Jan. 23, 2007, now Pat. No. 7,932,399.

(60) Provisional application No. 60/761,548, filed on Jan. 24, 2006.

(51) Int. Cl.
*A61K 31/4184* (2006.01)
(52) U.S. Cl.
USPC ...................................... 514/394
(58) Field of Classification Search
None
See application file for complete search history.

(56) References Cited

U.S. PATENT DOCUMENTS

| 3,987,182 | A  | 10/1976 | Gold |
| 4,213,994 | A  | 7/1980  | Gebert et al. |
| 7,566,733 | B2 | 7/2009  | Ng et al. |
| 7,932,399 | B2 | 4/2011  | Alford, Jr. et al. |

FOREIGN PATENT DOCUMENTS

| CA | 2582356 A1 | 4/2006 |
| EP | 583 665 A2 | 2/1994 |
| WO | WO 2006/039243 A1 | 4/2006 |

OTHER PUBLICATIONS

Golub et al., Science, vol. 286, Oct. 15, 1999, pp. 531-537.*
McOmie, J., "Protective Groups in Organic Chemistry", (1973) Title Page and Table of Contents.
T.W. Greene & P.G.M. Wutz (eds.), Protective Groups in Organic Synthesis, $2^{nd}$ edition, Wiley Interscience, (1991), pp. 473.
Bundgaard, H., "Design of Prodrugs", (1985), Table of Contents.
Basaria, S. et al.: Anabolic-Androgenic Steroid Therapy in the Treatment of Chronic Diseases; The J. of Clin. Endocrinology & Metab (2001), 86(11), pp. 5108-5117.
Newling, D.W.: Anti-androgens in the treatment of prostate cancer; Br. J. Urology (1996) 77(6), pp. 776-784.
Shahidi, N.T.: A Review of the Chemistry, Biological Action, and Clinical Applications of Anabolic-Androgenic Steroids; Clin. Therapeutics (2001), 23(9), pp. 1355-1390.
Murphy, K.D., "Effects of long-term oxandrolone administration in severely burned children", Surgery (2004), 136(2), pp. 219-224.
International Search Report PCT/US2007/060883, mailed Jul. 11, 2007.

* cited by examiner

*Primary Examiner* — Laura L. Stockton

(57) ABSTRACT

The present invention is directed to a novel 2-substituted benzimidazole derivatives, pharmaceutical compositions containing them and their use in the treatment of disorders and conditions modulated by the androgen receptor.

13 Claims, No Drawings

2-SUBSTITUTED BENZIMIDAZOLES AS SELECTIVE ANDROGEN RECEPTOR MODULATORS (SARMS)

CROSS REFERENCE TO RELATED APPLICATIONS

This application is a divisional of U.S. application Ser. No. 11/626,030, filed Jan. 23, 2007, now issued as U.S. Pat. No. 7,932,399; which in turn is a national stage application of International Patent Application No. PCT/EP2007/060883, filed Jan. 23, 2007, which application claims priority from U.S. Provisional Application No. 60/761,548, filed Jan. 24, 2006 the entire disclosures of which are hereby incorporated in their entirety.

FIELD OF THE INVENTION

The present invention is directed to novel 2-substituted benzimidazole derivatives, pharmaceutical compositions containing them and their use in the treatment of disorders and conditions modulated by the androgen receptor. More particularly, the compounds of the present invention are useful in the treatment of for example, prostate carcinoma, benign prostatic hyperplasia (BPH), hirsutism, alopecia, anorexia nervosa, breast cancer, acne, AIDS, cachexia, andropause, osteopenia, osteoporosis, female sexual dysfunction, male sexual dysfunction, as a libido enhancer, as a male contraceptive, as a male performance enhancer and/or for muscle replacement in burn recovery.

BACKGROUND OF THE INVENTION

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to 5α-dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatotoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, antagonists of the androgen receptor could be employed in the treatment of prostate cancer, benign prostatic hyperplasia, hirsutism in women, alopecia, anorexia nervosa, breast cancer and acne. Agonists of the androgen receptor could be employed in male contraception, male performance enhancement, as well as in the treatment of cancer, AIDS, cachexia, and other disorders. Additionally, agonists of the androgen receptor are useful in promoting burn recovery (Murphy, K. D., Suchmore, T., Micak, R. P., Chinkes, D. L., Klein, G. L., Herndon, D. N., *Effects of long-term oxandrolone administration in severely burned children*, Surgery, (2004), 136 (2), pp 219-224).

Nonetheless, there exists a need for small molecule, non-steroidal antagonists of the androgen receptor. We now describe a novel series of 2-substituted benzimidazole derivatives useful as androgen receptor modulators.

SUMMARY OF THE INVENTION

The present invention is directed to a compound of formula (I)

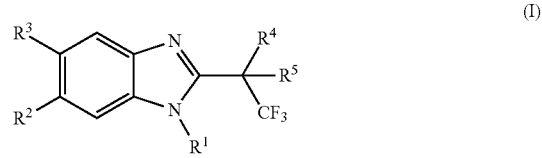

wherein $R^1$ is selected from the group consisting of hydrogen, lower alkyl, —(CH$_2$)—(C$_{2-4}$alkenyl), —(CH$_2$)—(C$_{2-4}$alkynyl), fluorinated lower alkyl, -(lower alkyl)-CN, —(CH$_2$)-heteroaryl, —(CH$_2$)-aryl, —SO$_2$-(lower alkyl), —SO$_2$-(phenyl), —SO$_2$-(tolyl), —(CH$_2$)-(fluorinated lower alkyl), -(lower alkyl)-C(O)—O-(lower alkyl), -(lower alkyl)-O-(lower alkyl), -(lower alkyl)-S(O)$_{0-2}$-(lower alkyl) and -(lower alkyl)-O—Si(CH$_3$)$_2$(t-butyl);

$R^2$ and $R^3$ are each independently selected from the group consisting of halogen, hydroxy, carboxy, lower alkyl, halogen substituted lower alkyl, lower alkoxy, halogen substituted lower alkoxy, cyano, nitro, amino, lower alkylamino, di(lower alkyl)amino, —C(O)-(lower alkyl), —C(O)-(lower alkoxy), —C(O)—NR$^A$R$^B$, —S(O)$_{0-2}$-(lower alkyl), —SO$_2$—NR$^A$R$^B$, —N(R$^A$)—C(O)-(lower alkyl) and —N(R$^A$)—C(O)-(halogen substituted lower alkyl);

wherein each R$^A$ and R$^B$ is independently selected from hydrogen or lower alkyl;

R$^4$ is selected from the group consisting of alkenyl, alkynyl, aryl, —(C$_{2-4}$alkyl)-aryl, heteroaryl and —(C$_{2-4}$alkyl)-heteroaryl;

wherein the alkenyl or alkynyl is optionally substituted with one or more substituents independently selected from the group consisting of halogen, hydroxy, carboxy, cyano, nitro, NR$^E$R$^F$, NR$^E$—C(O)-lower alkyl and phenyl; wherein R$^E$ and R$^F$ are each independently selected from hydrogen or lower alkyl; and wherein the phenyl (substituent on the alkenyl or alkynyl) is optionally substituted with one to four substituents independently selected from the group consisting of halogen, lower alkyl, lower alkoxy, hydroxy, carboxy, cyano, nitro, amino, (lower alkyl)amino and di(lower alkyl)amino;

wherein the aryl or heteroaryl, whether alone or as part of a substituent group is optionally substituted with one or more substituents independently selected from the group consisting of halogen, hydroxy, carboxy, lower alkyl, lower alkoxy, fluorinated lower alkyl, fluorinated lower alkoxy, phenoxy, cyano, nitro, $NR^CR^D$ and -(lower alkyl)-$NR^BR^C$, —C(O)-(lower alkyl), —C(O)-(lower alkoxy), —C(O)—$NR^CR^D$, —N($R^C$)—C(O)-(lower alkyl), —N($R^C$)—C(O)-(halogen substituted lower alkyl), —S(O)$_{0-2}$-(lower alkyl) and —SO$_2$—$NR^CR^D$; wherein each $R^C$ and $R^D$ is independently selected from hydrogen or lower alkyl;

$R^5$ is $OR^6$; wherein $R^6$ is selected from the group consisting of hydrogen, lower alkyl and —C(O)-(lower alkyl);

alternatively, $R^4$ and $R^5$ are taken together with the atom to which they are bound to form a ring structure selected from the group consisting of 2-pyrrolidinyl, 2-tetrahydro-furanyl, 2-(2,5-dihydro-1H-pyrrolyl), 2-(2,5-dihydro-furanyl), 2-imidazolidinyl, 2-oxazolidinyl, 2-[1,3]dioxolanyl, 2-piperidinyl, 6-(1,2,3,6-tetrahydro-pyridinyl), 2-(1,2,3,6-tetrahydro-pyridinyl), 2-tetrahydropyranyl, 6-(3,6-dihydro-2H-pyranyl), 2-(3,6-dihydro-2H-pyranyl), 2-(hexahydro-pyrimidinyl), 2-[1,3]oxazinanyl and 2-[1,3]dioxanyl;

wherein the ring structure is optionally substituted with one or more substituents independently selected from the group consisting of lower alkyl, -(lower alkyl)-OH and -(lower alkyl)-(halogen);

and pharmaceutically acceptable salts thereof.

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating disorders and conditions modulated by the androgen receptor comprising administering to a subject in need thereof, a therapeutically effective amount of any of the compounds or pharmaceutical compositions described herein.

An example of the invention is a method of treating an androgen receptor modulated disorder selected from the group consisting of prostate carcinoma, benign prostatic hyperplasia (BPH), hirsutism, alopecia, anorexia nervosa, breast cancer, acne, AIDS (Acquired Immune Deficiency Syndrome), cachexia, andropause, osteopenia, osteoporosis, female sexual dysfunction, male sexual dysfunction, diminished libido, male contraception, or for enhanced male performance or for muscle replacement in burn recovery, comprising administering to a subject in need thereof, a therapeutically effective amount of any of the compound of pharmaceutical compositions described herein.

Another example of the invention is a method of treating an androgen receptor modulated disorder selected from the group consisting prostate carcinoma, BPH, hirsutism, alopecia, breast cancer, acne and male contraception, comprising administering to a subject in need thereof, a therapeutically effective amount of any of the compound of pharmaceutical compositions described herein.

Another example of the invention is a method of treating an androgen receptor modulated disorder selected from the group consisting anorexia, AIDS, cachexia, andropause, osteopenia, osteoporosis, female sexual dysfunction, male sexual dysfunction, diminished libido, enhancing male performance, and muscle replacement in burn recovery, comprising administering to a subject in need thereof, a therapeutically effective amount of any of the compound of pharmaceutical compositions described herein.

Another example of the invention is the use of any of the compounds described herein in the preparation of a medicament for treating: (a) prostate carcinoma, (b) benign prostatic hyperplasia (BPH), (c) hirsutism, (d) alopecia, (e) anorexia nervosa, (f) breast cancer, (g) acne, (h) AIDS, (i) cachexia, (j) andropause, (k) osteopenia, (l) osteoporosis, (m) female sexual dysfunction, (n) male sexual dysfunction, (o) diminished libido, for (p) male contraception, for (q) enhanced male performance or for (r) muscle replacement in burn recovery, in a subject in need thereof.

DETAILED DESCRIPTION OF THE INVENTION

The present invention is directed to a process for the preparation of compound of formula (I)

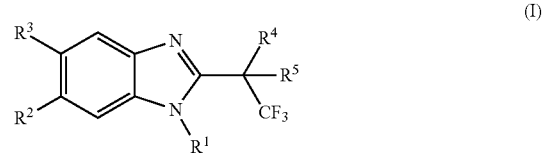

wherein $R^1$, $R^2$, $R^3$, $R^4$ and $R^5$ are as herein defined. The compounds of the present invention are useful as selective androgen receptor modulators for the treatment of disorders mediated by at least one androgen receptor selected from the group consisting of prostate carcinoma, benign prostatic hyperplasia (BPH), hirsutism, alopecia, anorexia nervosa, breast cancer, acne, AIDS, cachexia, andropause, osteopenia, osteoporosis, female sexual dysfunction, male sexual dysfunction and diminished libido, or for male contraception, for enhanced male performance or for muscle replacement in burn recovery.

Preferably, the disorder modulated by a least one androgen receptor is selected from the group consisting of cachexia, andropause, osteoperosis, osteopenia and muscle replacement in burn recovery, more preferably, the disorder mediated by at least one androgen receptor is selected from the group consisting of cachexia, andropause, osteoperosis and osteopenia.

In an embodiment, the present invention is directed to compounds of formula (I) which are antagonists of an androgen receptor. In another embodiment, the present invention is directed to compounds of formula (I) which are agonists of an androgen receptor. In another embodiment, the present invention is directed to compounds of formula (I) which exhibit tissue selective agonism and antagonism of an androgen receptor.

In an embodiment, the present invention is directed to compounds of formula (I) which are useful for the treatment of prostate cancer, benign prostatic hyperplasia, hirsutism in women, alopecia, anorexia nervosa, breast cancer and acne. In another embodiment, the present invention is directed to compounds of formula (I) which are useful for male contraception, male performance enhancement, and/or for the treatment of cancer, AIDS, cachexia, and/or for promoting muscle replacement in burn recovery.

In an embodiment of the present invention, $R^1$ is selected from the group consisting of hydrogen, lower alkyl, -(lower alkyl)-CN, —(CH$_2$)—(C$_{2-4}$alkenyl), —(CH$_2$)—(C$_{2-4}$alkynyl), fluorinated lower alkyl, —(CH$_2$)-heteroaryl, —(CH$_2$)-aryl, —(CH$_2$)-(fluorinated lower alkyl), -(lower alkyl)-C(O)—O-(lower alkyl), -(lower alkyl)-O-(lower alkyl), and -(lower alkyl)-O—Si(CH$_3$)$_2$(t-butyl).

In another embodiment of the present invention, R$^1$ is selected from the group consisting of hydrogen, lower alkyl, -(lower alkyl)-CN, —(CH$_2$)-heteroaryl, —(CH$_2$)—(C$_{2-4}$alkenyl), —(CH$_2$)—(C$_{2-4}$alkynyl), -(lower alkyl)-C(O)O-(lower alkyl) and -(lower alkyl)-O—Si(CH$_3$)$_2$(t-butyl). In another embodiment of the present invention, R$^1$ is selected from the group consisting of hydrogen, methyl, ethyl, cyano-methyl-, 2-pyridyl-methyl-, allyl, 1-propyn-3-yl, methoxy-carbonyl-methyl- and t-butyl-dimethyl-silyloxy-ethyl-.

In another embodiment of the present invention, R$^1$ is selected from the group consisting of hydrogen, methyl, ethyl, cyano-methyl-, 2-pyridyl-methyl-, allyl, 1-propyn-3-yl, methoxy-carbonyl-methyl- and t-butyl-dimethyl-silyloxy-ethyl-. In another embodiment of the present invention, R$^1$ is selected from the group consisting of hydrogen, ethyl, cyano-methyl-, allyl and 1-propyn-3-yl.

In another embodiment of the present invention, R$^1$ is selected from the group consisting of hydrogen and lower alkyl. In another embodiment of the present invention, R$^1$ is selected from the group consisting of hydrogen and methyl. In another embodiment of the present invention, R$^1$ is hydrogen.

In an embodiment of the present invention, R$^2$ and R$^3$ are each independently selected from the group consisting of halogen, hydroxy, carboxy, lower alkyl, halogen substituted lower alkyl, cyano, nitro, amino, lower alkylamino, di(lower alkyl)amino, —C(O)-(lower alkyl), —C(O)-(lower alkoxy), —C(O)—NR$^A$R$^B$, —N(R$^A$)—C(O)-(lower alkyl) and —N(R$^A$)—C(O)-(halogen substituted lower alkyl); wherein each R$^A$ and R$^B$ is independently selected from hydrogen methyl or ethyl.

In another embodiment of the present invention, R$^2$ and R$^3$ are each independently selected from the group consisting of halogen, cyano and halogen substituted lower alkyl. In another embodiment of the present invention, R$^2$ and R$^3$ are each independently selected from the group consisting of chloro, trifluoromethyl and cyano. In another embodiment of the present invention, R$^2$ and R$^3$ are each chloro;

In another embodiment of the present invention, R$^2$ and R$^3$ are each independently selected from the group consisting of halogen and halogen substituted lower alkyl. In another embodiment of the present invention, R$^2$ and R$^3$ are each independently selected from the group consisting of chloro and trifluoromethyl.

In an embodiment of the present invention, R$^2$ is selected from the group consisting of chloro and trifluoromethyl. In an embodiment of the present invention, R$^3$ is selected from the group consisting of chloro and cyano. In another embodiment of the present invention, R$^3$ is chloro;

In an embodiment of the present invention, R$^4$ is selected from the group consisting of alkenyl, alkynyl, aryl, —(C$_{2-4}$alkyl)-aryl, heteroaryl and —(C$_{2-4}$alkyl)-heteroaryl; wherein the alkenyl or alkynyl is optionally substituted with one to two (preferably one) substituents independently selected from the group consisting of halogen, hydroxy, carboxy, cyano, nitro, NR$^E$R$^F$, NR$^E$—C(O)-lower alkyl and phenyl; wherein R$^E$ and R$^F$ are each independently selected from hydrogen or lower alkyl; and wherein the phenyl is optionally substituted with one to two (preferably one) substituents independently selected from the group consisting of halogen, lower alkyl, lower alkoxy, hydroxy, carboxy, cyano, nitro, amino, (lower alkyl)amino and di(lower alkyl)amino; and wherein the aryl or heteroaryl, whether alone or as part of a substituent group is optionally substituted with one to two substituents (preferably one) independently selected from the group consisting of halogen, hydroxy, carboxy, lower alkyl, lower alkoxy, fluorinated lower alkyl, fluorinated lower alkoxy, phenoxy, cyano, nitro, NR$^C$R$^D$, -(lower alkyl)-NR$^B$R$^D$, —C(O)-(lower alkyl) and —C(O)-(lower alkoxy); and wherein each R$^C$ and R$^D$ is independently selected from hydrogen or lower alkyl. In another embodiment of the present invention, R$^4$ is selected from the group consisting of alkenyl, alkynyl and aryl; wherein the aryl is optionally substituted as herein defined. In another embodiment of the present invention, R$^4$ is selected from the group consisting of alkenyl and alkynyl.

In another embodiment of the present invention, R$^4$ is selected from the group consisting of vinyl, (+)-vinyl, (−)-vinyl, allyl, (+)-allyl, (−)-allyl, 2-methyl-allyl, 2-propen-3-yl, Z-2-propen-3-yl, E-2-propen-3-yl, 3-methyl-1-propen-3-yl, 2-carboxy-1-propen-3-yl, 3-phenyl-1-propen-3-yl, 3,3-dimethyl-1-propen-3-yl, 2,3-dimethyl-2-propen-3-yl, 2-methyl-2-propen-3-yl), isopropenyl, propa-1,2-dien-3-yl, 3-methyl-propa-1,2-dien-3-yl, 3-ethyl-propa-1,2-dien-3-yl), 1-buten-4-yl, 1-propyn-3-yl, (+)-1-propyn-3-yl, (−)-1-propyn-3-yl, 2-propyn-3-yl, 1-hydroxy-2-propyn-3-yl, 1-phenyl-1-propyn-3-yl, 2-butyn-4-yl and phenyl.

In another embodiment of the present invention, R$^4$ is selected from the group consisting of vinyl, allyl, (+)-allyl, (−)-allyl, 2-methyl-allyl, 2-propen-3-yl, Z-2-propen-3-yl, E-2-propen-3-yl, 3-methyl-1-propen-3-yl, 3-phenyl-1-propen-3-yl, 3,3-dimethyl-1-propen-3-yl, 2,3-dimethyl-2-propen-3-yl, 2-methyl-2-propen-3-yl, isopropenyl, propa-1,2-dien-3-yl, 3-methyl-propa-1,2-dien-3-yl, 3-ethyl-propa-1,2-dien-3-yl, 1-buten-4-yl, 1-propyn-3-yl, (+)-1-propyn-3-yl, (−)-1-propyn-3-yl, 2-propyn-3-yl and phenyl. In another embodiment of the present invention, R$^4$ is selected from the group consisting of vinyl, (+)-vinyl, allyl, Z-2-propen-3-yl, propa-1,2-dien-3-yl, 1-propyn-3-yl, (+)-1-propyn-3-yl and (−)-1-propyn-3-yl. In another embodiment of the present invention, R$^4$ is selected from the group consisting of isopropenyl, Z-2-propen-3-yl and (+)-vinyl.

In an embodiment of the present invention, R$^4$ is selected from the group consisting of alkenyl, alkynyl and aryl; wherein the alkenyl is optionally substituted with a substituent selected from the group consisting of hydroxy, carboxy and phenyl.

In another embodiment of the present invention, R$^4$ is selected from the group consisting of vinyl, (+)-vinyl, (−)-vinyl, allyl, (+)-allyl, (−)-allyl, 2-methyl-allyl, 2-propen-3-yl, Z-2-propen-3-yl, E-2-propen-3-yl, 3-methyl-1-propen-3-yl, 2-carboxy-1-propen-3-yl, 3-phenyl-1-propen-3-yl, 3,3-dimethyl-1-propen-3-yl, 2,3-dimethyl-2-propen-3-yl, 2-methyl-2-propen-3-yl), isopropenyl, propa-1,2-dien-3-yl, 3-methyl-propa-1,2-dien-3-yl, 3-ethyl-propa-1,2-dien-3-yl, 1-buten-4-yl, 1-propyn-3-yl, 2-propyn-3-yl, (+)-1-propyn-3-yl, (−)-1- propyn-3-yl, 1-hydroxy-2-propyn-3-yl, 1-phenyl-1-propyn-3-yl, 2-butyn-4-yl and phenyl.

In another embodiment of the present invention, $R^4$ is selected from the group consisting of isopropenyl, Z-2-propen-3-yl and (+)-vinyl.

In an embodiment of the present invention, $R^5$ is $OR^6$; wherein $R^6$ is selected from the group consisting of hydrogen, methyl, ethyl, —C(O)-methyl and —C(O)-ethyl. In another embodiment of the present invention, $R^5$ is OH.

In an embodiment of the present invention, $R^4$ and $R^5$ are taken together with the atom to which they are bound to form a ring structure selected from the group consisting of 2-pyrrolidinyl, 2-tetrahydro-furanyl, 2-(2,5-dihydro-1H-pyrrolyl), 2-(2,5-dihydro-furanyl), 2-imidazolidinyl, 2-oxazolidinyl, 2-[1,3]dioxolanyl, 2-piperidinyl, 6-(1,2,3,6-tetrahydro-pyridinyl), 2-(1,2,3,6-tetrahydro-pyridinyl), 2-tetrahydropyranyl, 6-(3,6-dihydro-2H-pyranyl), 2-(3,6-dihydro-2H-pyranyl), 2-(hexahydro-pyrimidinyl), 2-[1,3]oxazinanyl and 2-[1,3]dioxanyl; wherein the ring structure is optionally substituted with one or more substituents (preferably one to two, more preferably one substituent) independently selected from the group consisting of $C_{1-2}$alkyl, —($C_{1-2}$alkyl)-OH and —($C_{1-2}$alkyl)-halogen.

In another embodiment of the present invention, $R^4$ and $R^5$ are taken together with the atom to which they are bound to form a ring structure selected from the group consisting of 2,5-dihydro-furanyl, 2-tetrahydrofuranyl, 2-[1,3]-dioxolanyl, 2-[1,3]dioxanyl, 2-imidazolyl and 2-oxazolidinyl; wherein the ring structure is optionally substituted with one or more substituents (preferably one to two, more preferably one substituent) independently selected from the group consisting of methyl, ethyl, hydroxymethyl, hydroxyethyl, and —($C_{1-2}$alkyl)-halogen.

In another embodiment of the present invention, $R^4$ and $R^5$ are taken together with the atom to which they are bound to form a ring structure selected from the group consisting of 2,5-dihydro-furanyl, 2-tetrahydrofuranyl, 2-[1,3]-dioxolanyl, 2-(4-hydroxymethyl-[1,3]dioxalanyl), 2-(4-chloromethyl-[1,3]dioxalanyl, 2-[1,3]dioxanyl, 2-imidazolyl and 2-oxazolidinyl.

In another embodiment of the present invention, $R^4$ and $R^5$ are taken together with the atom to which they are bound to form a ring structure selected from the group consisting of 2-tetrahydrofuranyl, 2-[1,3]-dioxolanyl, 2-(4-hydroxymethyl-[1,3]dioxalanyl), 2-(4-chloromethyl-[1,3]dioxalanyl, 2-[1,3]dioxanyl, 2-imidazolyl and 2-oxazolidinyl.

In another embodiment of the present invention, $R^4$ and $R^5$ are taken together with the atom to which they are bound to form a ring structure selected from the group consisting of 2,5-dihydro-furanyl and 2-tetrahydrofuranyl. In another embodiment of the present invention, $R^4$ and $R^5$ are taken together with the atom to which they are bound to form 2-[1,3]dioxalanyl.

Additional embodiments of the present invention, include those wherein the substituents selected for one or more of the variables defined herein (i.e. $R^1$, $R^2$, $R^3$, $R^4$, $R^5$, $R^6$) are independently selected to be any individual substituent or any subset of substituents selected from the complete list as defined herein.

Additional embodiments of the present invention include any single compound or subset of compounds selected from the representative compounds listed in Tables 1-2 below.

Representative compounds of the present invention are as listed in Table 1 to 2 below. Unless otherwise noted, wherein a stereogenic center is present in the listed compound, the compound was prepared as a mixture of stereo-configurations. Where a stereogenic center is present, the (+)- and (−)-designations are intended to indicate that the exact stereo-configuration of the center has not been determined, but the direction of the optical rotation has been determined.

TABLE 1

Representative Compounds of Formula (I)

| ID No. | $R^1$ | $R^2$ | $R^3$ | $R^4$ |
|---|---|---|---|---|
| 1 | H | chloro | chloro | allyl |
| 2 | H | chloro | chloro | 1-propyn-3-yl |
| 3 | H | chloro | chloro | propa-1,2-dien-3-yl |
| 4 | H | chloro | chloro | vinyl |
| 6 | H | chloro | chloro | 3-methyl-propa-1,2-dien-3-yl |
| 8 | H | chloro | chloro | 2-propyn-3-yl |
| 9 | H | chloro | chloro | isopropenyl |
| 10 | H | chloro | chloro | phenyl |
| 13 | H | chloro | chloro | 2-methyl-allyl |
| 14 | H | chloro | chloro | 2-methyl-2-propen-3-yl |
| 15 | H | chloro | chloro | Z-2-propen-3-yl |
| 16 | H | chloro | chloro | E-2-propen-3-yl |
| 17 | H | chloro | chloro | 1-hydroxy-2-propyn-3-yl |
| 23 | H | chloro | chloro | (+)-allyl |
| 24 | H | chloro | chloro | (−)-allyl |
| 25 | H | chloro | chloro | 3,3-dimethyl-1-propen-3-yl |
| 26 | H | chloro | chloro | 3-methyl-1-propen-3-yl |
| 27 | H | chloro | chloro | 2-carboxy-1-propen-3-yl |
| 28 | H | chloro | chloro | 3-phenyl-1-propen-3-yl |
| 31 | H | chloro | chloro | (+)-1-propyn-3-yl |
| 32 | H | chloro | chloro | (−)-1-propyn-3-yl |
| 33 | H | chloro | chloro | 2-butyn-1-yl |
| 34 | H | chloro | chloro | 1--phenyl-1-propyn-3-yl |
| 35 | methyl | chloro | chloro | 1-propyn-3-yl |
| 36 | methyl | chloro | chloro | (+)-1-propyn-3-yl |
| 37 | methyl | chloro | chloro | (−)-1-propyn-3-yl |
| 38 | H | trifluoro-methyl | cyano | allyl |
| 39 | H | trifluoro-methyl | cyano | 1-propyn-3-yl |
| 40 | H | chloro | chloro | 1-buten-4-yl |
| 41 | H | trifluoro-methyl | cyano | 3-methyl-propa-1,2-dien3-yl |
| 42 | H | chloro | chloro | 2,3-dimethyl-2-propen-3-yl |
| 43 | H | chloro | chloro | (+)-vinyl |
| 44 | H | chloro | chloro | (−)-vinyl |
| 62 | H | chloro | chloro | 3-ethyl-propa-1,2-dien-3-yl |

TABLE 2

Representative Compounds of Formula (I)

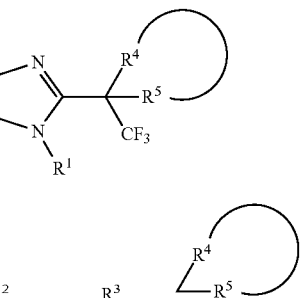

| No. | R¹ | R² | R³ | R⁴-R⁵ |
|---|---|---|---|---|
| 45 | H | chloro | chloro | 2,5-dihydro-furanyl |
| 46 | H | chloro | chloro | 2-tetrahydro-furanyl |
| 47 | H | chloro | chloro | 2-[1,3]dioxolanyl |
| 48 | 2-pyridyl-methyl- | chloro | chloro | 2-[1,3]dioxolanyl |
| 49 | H | chloro | chloro | 2-(4-hydroxymethyl-[1,3]dioxalanyl) |
| 50 | H | chloro | chloro | 2-(4-chloromethyl-[1,3]dioxalanyl) |
| 51 | H | chloro | chloro | 2-[1,3]dioxanyl |
| 52 | methyl | chloro | chloro | 2-(4-hydroxymethyl-[1,3]dioxalanyl) |
| 53 | cyano-methyl- | chloro | chloro | 2-(4-chloromethyl-[1,3]dioxalanyl) |
| 54 | 1-propyn-3-yl | chloro | chloro | 2-[1,3]dioxolanyl |
| 55 | allyl | chloro | chloro | 2-[1,3]dioxolanyl |
| 56 | ethyl | chloro | chloro | 2-[1,3]dioxolanyl |
| 57 | methoxy-carbonyl-methyl- | chloro | chloro | 2-[1,3]dioxolanyl |
| 58 | t-butyl-dimethyl-silyloxy-ethyl- | chloro | chloro | 2-[1,3]dioxolanyl |
| 59 | H | trifluoro-methyl | cyano | 2-[1,3]dioxolanyl |
| 60 | H | chloro | chloro | 2-imidazolidinyl |
| 61 | H | chloro | chloro | 2-oxazolidinyl |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, the term "alkenyl" whether used alone or as part of a substituent group, include straight and branched carbon chains, wherein the carbon chain contains at least one, preferably one to two, more preferably one double bond. For example, alkenyl radicals include, but are not limited to allyl, 1-propen-3-yl, 1-buten-4-yl, propa-1,2-dien-3-yl, and the like. Unless otherwise noted, "lower" when used with alkenyl means a carbon chain composition of 2-4 carbon atoms.

As used herein, the term "alkynyl" whether used alone or as part of a substituent group, include straight and branched carbon chains, wherein the carbon chain contains at least one, preferably one to two, more preferably one triple bond. For example, alkynyl radicals include, but are not limited to vinyl, 1-propyn-3-yl, 2-butyn-4-yl, and the like. Unless otherwise noted, "lower" when used with alkynyl means a carbon chain composition of 2-4 carbon atoms.

As used herein, unless otherwise noted, the term "halogen substituted alkyl" or "halogen substituted lower alkyl" shall mean any alkyl or lower alkyl group as defined above substituted with a least one halogen atom selected from the group consisting of F, Cl, Br or I, preferably F, Cl or Br, more preferably F or Cl, most preferably F. Similarly, as used herein, unless otherwise noted, the term "fluorinated alkyl" or "fluorinated lower alkyl" shall mean any alkyl or lower alkyl group as defined above substituted with a least one fluoro atom. Suitable examples include but are not limited to —$CF_3$, —$CH_2$—$CF_3$, —$CF_2$—$CF_2$—$CF_2$—$CF_3$, and the like. Preferably, the fluorinated alkyl or fluorinated lower alkyl is —$CF_3$.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, the term "halogen substituted alkoxy" or "halogen substituted lower alkoxy" shall mean any alkoxy or lower alkoxy group as defined above substituted with a least one halogen atom selected from the group consisting of F, Cl, Br or I, preferably F, Cl or Br, more preferably F or Cl, most preferably F. Similarly, as used herein, unless otherwise noted, the term "fluorinated alkoxy" or "fluorinated lower alkoxy" shall mean any alkoxy or lower alkoxy group as defined above substituted with a least one fluoro atom. Suitable examples include but are not limited to —$OCF_3$, —$OCH_2$—$CF_3$, —$OCF_2$—$CF_2$—$CF_2$—$CF_3$, and the like. Preferably, the fluorinated alkoxy or fluorinated lower alkoxy is —$OCF_3$.

As used herein, unless otherwise noted, "aryl" shall refer to unsubstituted carbocylic aromatic groups such as phenyl, naphthyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the notation "*" shall denote the presence of a stereogenic center.

When a particular group is "substituted" (e.g., alkenyl, aryl, heteroaryl, etc), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives-groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-($C_1$-$C_6$alkyl)-aminocarbonyl-($C_1$-$C_6$alkyl)" substituent refers to a group of the formula

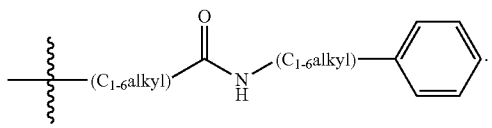

Abbreviations used in the specification, particularly the Schemes and Examples, are as follows:
AIDS=Acquired Immune Deficiency Syndrome
AR=Androgen Receptor
BPH=Benign Prostatic Hyperplasia
n-BuLi=n-Butyl Lithium
DCM=Dichloromethane
DHT=5α-Dihydrotestosterone
DMF=N,N-Dimethylformamide
DMSO=Dimethylsulfoxide
$Et_2O$=Diethyl ether
EtOAc=Ethyl acetate
HPLC=High Pressure Liquid Chormatography
NMR=Nuclear Magnetic Resonance
PPTS=Pyridinium p-toluenesulfonate
pTsOH=p-Toluene sulfonic acid
TBAHS or $Bu_4NHSO_4$=Tetra-n-butylammonium hydrogen sulfate
TEMPO=2,2,6,6,-Tetramethyl-1-piperidinyloxy, free radical
THF=Tetrahydrofuran As used herein, unless otherwise noted, the term an "androgen modulator" shall mean any compound which exhibits tissue selective agonist and/or antagonist activity. For example, an androgen modulator may be a compound which exhibits agonist activity in muscle tissue and antagonist activity in prostate tissue (e.g. for the treatment of cachexia). Further, an androgen modulator may be a compound that exhibits varying amounts of agonist or antagonist activity depending on the tissue type.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Compounds of formula (I) wherein $R^1$ is hydrogen and $R^5$ is OH may be prepared according to the process outlined in Scheme 1.

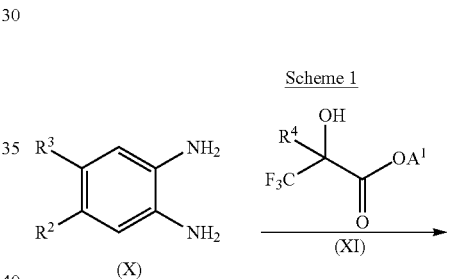

Accordingly, a suitably substituted compound of formula (X), a known compound or compound prepared by known methods, is reacted with a suitably substituted compound of formula (XI), wherein $A^1$ is lower alkyl, a known compound or compound prepared by known methods, in the presence of a Lewis acid such as $AlCl(CH_2CH_3)_2$, $Al(CH_3)_3$, $TiCl_4$, and the like, in an organic solvent such as toluene, xylenes, and the like, at a temperature greater than about room temperature, preferably at a temperature of about 80° C., more preferably, at about reflux temperature, to yield the corresponding compound of formula (Ia).

Compounds of formula (I) wherein $R^1$ is hydrogen and $R^5$ is OH may alternatively be prepared according to the process outlined in Scheme 2 below.

Scheme 2

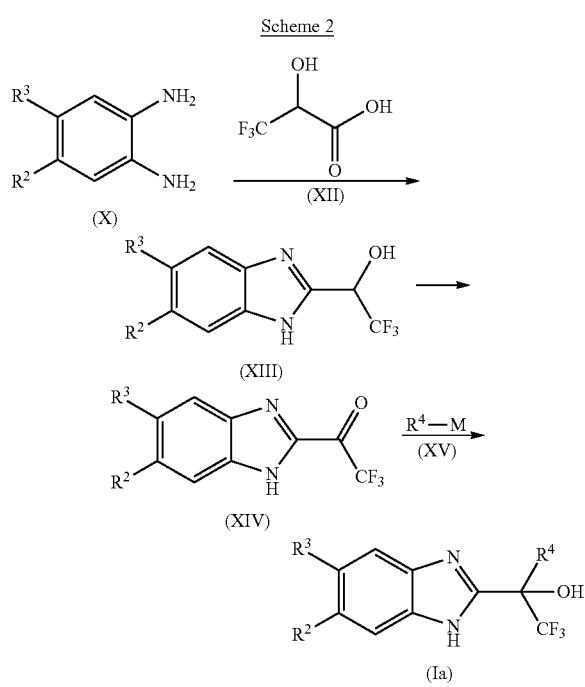

Accordingly, a suitably substituted compound of formula (X), a known compound or compound prepared by known methods, is reacted with a suitably substituted compound of formula (XII), in the presence of an acid such as HCl, $H_2SO_4$, HBr, and the like, in water; or in the presence of polyphosphoric acid (PPA), neat (i.e. in the absence of additional solvent); at a temperature greater than about room temperature, preferably at about reflux temperature, to yield the corresponding compound of formula (XIII).

The compound of formula (XIII) is reacted with a suitably selected oxidizing agent, to yield the corresponding compound of formula (XIV). For example, the compound of formula (XIII) may be reacted with a mixture of bleach and TEMPO, in the presence of a phase transfer catalyst such as TBAHS, in the presence of a salt such as KBr, in a two-phase mixture of water and organic solvent (such as ethyl acetate, DCM, and the like), to yield the corresponding compound of formula (XIV). Alternatively, the compound of formula (XIII) may be reacted with a mixture of $CrO_3$ and $H_2SO$ in a solvent such as water, DCM, and the like, to yield the corresponding compound of formula (XIV). Alternatively still, the compound of formula (XIII) may be reacted with Dess-Martin periodinane, in an organic solvent such as DCM, benzene, and the like, to yield the corresponding compound of formula (XIV).

Preferably, the compound of formula (XIV) is dried to remove any hydrated water/any hydrate component.

The compound of formula (XIV) is reacted with a suitably substituted compound of formula (XV), wherein M is MgCl, MgBr, MgI or Li, a known compound or compound prepared by known methods, to yield the corresponding compound of formula (Ia).

For example, wherein the compound of formula (XV) M is MgCl, MgBr, MgI or Li, the compound of formula (XIV) is reacted with the compound of formula (XV), in an anhydrous organic solvent such as THF, diethyl ether, and the like, preferably at a temperature less than about room temperature, more preferably, at about 0° C., to yield the corresponding compound of formula (Ia).

Alternatively, wherein the compound of formula (XV) M is Br, the compound of formula (XIV) is reacted with the compound of formula (XV), in the presence of in metal, in a mixture of an aqueous solution of pH from about 7 to about 4, preferably a pH from about 3 to about 4, and an organic solvent such as ethyl acetate, DCM, and the like, preferably at about room temperature, to yield the corresponding compound of formula (Ia).

One skilled in the art will recognize that wherein the compound of formula (XIV) is reacted with a compound of formula (XV) wherein M is MgCl, MgBr, MgI or Li, the compound of formula (XIV) is preferably dried prior to the reaction.

Preferably, the compound of formula (XIV) is reacted with a compound of formula (XV) wherein M is MgCl, MgBr, MgI or Li for the preparation of compounds of formula (I) wherein $R^4$ is alkyl, alkenyl, aryl, ($C_{2-4}$alkyl)-aryl, heteroaryl or -(lower alkyl)-heteroaryl.

Preferably, the compound of formula (XIV) is reacted with a compound of formula (XV) wherein M is Br for the preparation of compounds of formula (I) wherein $R^4$ is alkenyl, —(CH)-alkenyl or —($CH_2$)-alkynyl.

Compounds of formula (I) wherein $R^4$ and $R^5$ are taken together with the atoms to which they are bound to form a ring structure containing one heteroatom may be prepared according to the process outlined in Scheme 3 below.

Scheme 3

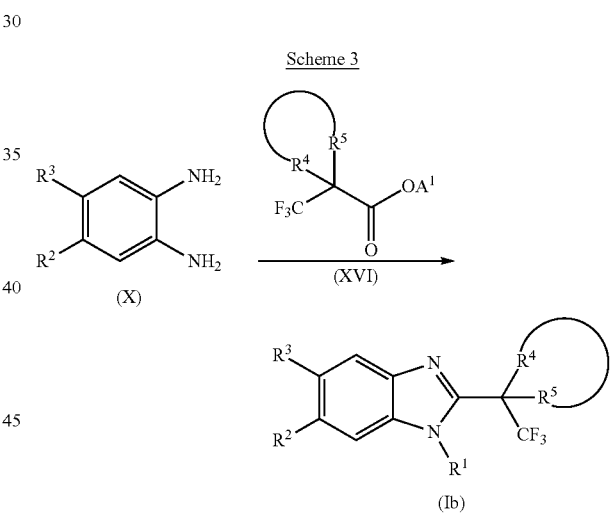

Accordingly, a suitably substituted compound of formula (X), a known compound or compound prepared by known methods, is reacted with a suitably substituted compound of formula (XVI), wherein $A^1$ is lower alkyl, a known compound or compound prepared by known methods, in the presence of a Lewis acid such as $AlCl(CH_2CH_3)_2$, $Al(CH_3)_3$, $TiCl_4$, and the like, in an organic solvent such as toluene, xylenes, and the like, at a temperature greater than about room temperature, preferably at a temperature of about 80° C., more preferably, at about reflux temperature, to yield the corresponding compound of formula (Ib).

Compounds of formula (I) wherein $R^4$ and $R^5$ are taken together with the atom to which they are bound to form a ring structure containing two O heteroatoms may alternatively be prepared according to the process outlined in Scheme 4 below.

Scheme 4

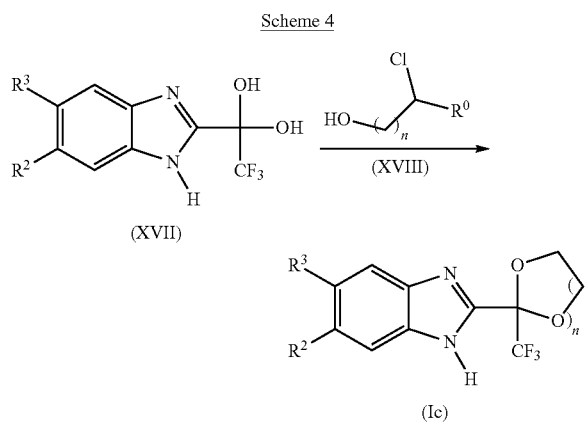

Scheme 6

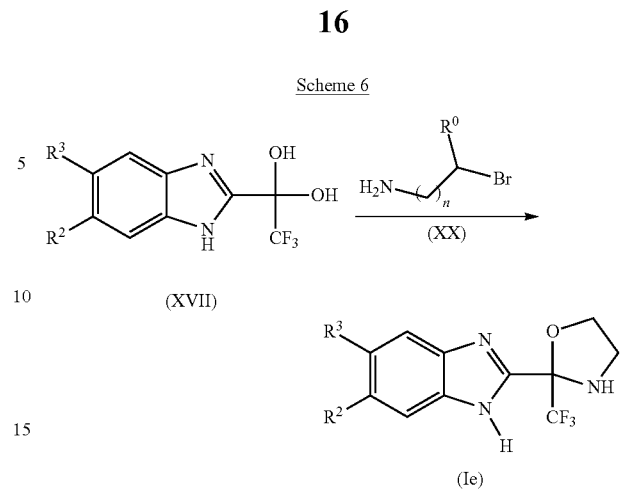

Accordingly, a suitably substituted compound of formula (XVII), a known compound or compound prepared according to known methods, is reacted with a suitably substituted compound of formula (XVIII), wherein $R^0$ is selected from the group consisting of hydrogen, lower alkyl, -(lower alkyl)-OH and -(lower alkyl)-(halogen), a known compound or compound prepared by known methods, in the presence of an inorganic base such as $K_2CO_3$, $Na_2CO_3$, $Cs_2CO_3$, and the like, in an organic solvent such as DMF, DMSO, and the like, to yield the corresponding compounds of formula (Ic).

Compounds of formula (I) wherein $R^4$ and $R^5$ are taken together with the atom to which they are bound to form a ring structure containing two N heteroatoms may be prepared according to the process outlined in Scheme 5 below.

Accordingly, a suitably substituted compound of formula (XVII) is reacted with a suitably substituted compound of formula (XX), wherein $R^0$ is selected from the group consisting of hydrogen, lower alkyl, -(lower alkyl)-OH and -(lower alkyl)-(halogen), in the presence of an inorganic base such as $K_2CO_3$, $Na_2CO_3$, $Cs_2CO_3$, and the like, in an organic solvent such as DMF, DMSO, and the like, to yield the corresponding compound of formula (Ie).

One skilled in the art will recognize that compounds of formula (I) wherein $R^4$ and $R^5$ are taken together with the atom to which they are bound to form a ring structure may alternatively be prepared according to the processes outlined in Schemes 4, 5 and 6 above, by substituting a suitably substituted compound of formula (XXI)

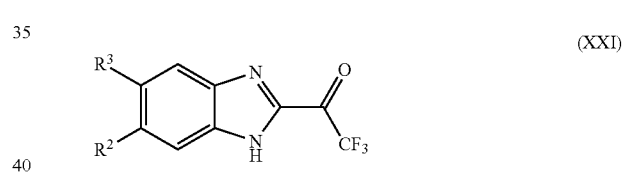

(XXI)

a known compound or compound prepared by known methods (for example as described in Example 2 which follows herein), for the compound of formula (XVII). One skilled in the art will recognize that the compound of formula (XXI) will equilibrate with the corresponding compound of formula (XVII) in the presence of water.

Compounds of formula (I) wherein $R^5$ is —$OR^6$ and $R^6$ is other than H can be prepared from the corresponding compound of formula (Ia), according to known methods, for example alkylation, acylation, reacting with a suitably substituted compound of the formula $R^1$—Br in the presence of NaH, and the like.

Scheme 5

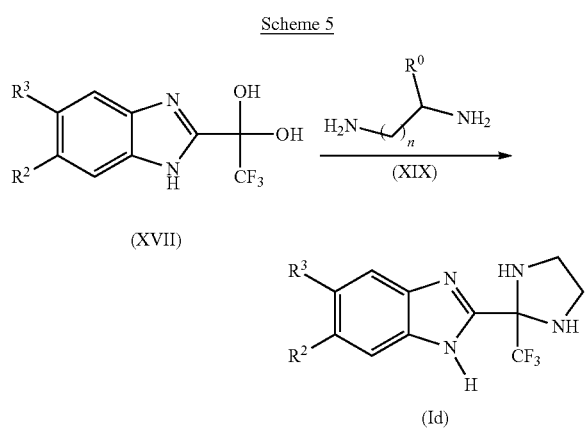

Accordingly, a suitably substituted compound of formula (XVII), a known compound or compound prepared by known methods is reacted with a suitably substituted compound of formula (XIX), wherein $R^0$ is selected from the group consisting of hydrogen, lower alkyl, -(lower alkyl)-OH and -(lower alkyl)-(halogen), a known compound or compound prepared by known methods, in the presence of a catalyst such as pTsOH, PPTS, and the like, in an organic solvent such as toluene, xylenes, and the like, at a temperature greater than about room temperature, preferably at about reflux temperature, to yield the corresponding compound of formula (Id).

Compounds of formula (I) wherein $R^4$ and $R^5$ are taken together with the atom to which they are bound to form a ring structure containing an O and a N heteroatom may alternatively be prepared according to the process outlined in Scheme 6 below.

Compounds of formula (I) wherein $R^1$ is other than H can be prepared from the corresponding compound of formula (Ia), according to known methods, for example by alkylation, acylation, sulfonylation, and the like.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01-500 mg and may be given at a dosage of from about 0.05-500 mg/kg/day, preferably from about 0.05-10 mg/kg/day, more preferably from about 0.1-5.0 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders or conditions modulated by the androgen receptor described in the present invention may also be carried out using a pharmaceutical composition comprising any of the compounds as defined herein and a pharmaceutically acceptable carrier. The pharmaceutical composition may contain between about 0.01 mg and 500 mg, preferably about 1 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders or conditions modulated by the androgen receptor is required.

The daily dosage of the products may be varied over a wide range from 0.01 to 500 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day. Preferably, the range is from about 0.5 to about 10.0 mg/kg of body weight per day, most preferably, from about 0.1 to about 5.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

1-(5,6-Dichloro-1H-benzoimidazol-2-yl)-2,2,2-trifluoro-ethanol

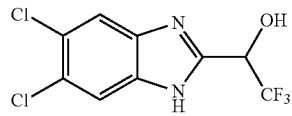 [SMILES: OC(c1nc2cc(Cl)c(Cl)cc2[nH]1)C(F)(F)F]

A 1-L 4-neck flask equipped with a thermocouple controller, an overhead mechanical stirrer, a condenser, and a nitrogen inlet/outlet adaptor was charged with 4,5-dichloro-1,2-phenylenediamine (71.3 g, 0.403 mol), trifluorolactic acid (87.0 g, 0.604 mol) and 4N HCl (340 mL). The reaction mixture was heated for 18 h at reflux (100° C.). The resulting solution was cooled to room temperature and then diluted with EtOAc (1 L) and $H_2O$ (1 L). The solution was slowly treated with $NaHCO_3$ (500 g) until pH 8-9. After the effervescence ceased, the phases were split and aqueous layer was back extracted with EtOAc (3×1 L). The combine organic phase was washed with $H_2O$ (1 L) and brine (1 L); dried over $MgSO_4$, filtered and evaporated to dryness to yield a crude residue. The crude residue was purified by flash chromatography using $SiO_2$ (2 kg) and 10% $EtOAc/CH_2Cl_2$ (2 L) and 20% $EtOAc/CH_2Cl_2$ (32 L) and the product dried in vacuo for 18 h at 60° C. to yield the title compound as a brownish solid.

Example 2

1-(5,6-Dichloro-1H-benzoimidazol-2-yl)-2,2,2-trifluoro-ethanone

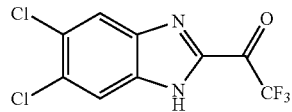 [SMILES: O=C(c1nc2cc(Cl)c(Cl)cc2[nH]1)C(F)(F)F]

A 3-L 4-neck flask equipped with a thermocouple controller, an overhead mechanical stirrer, an addition funnel, and a nitrogen inlet/outlet adaptor was charged with 1-(5,6-dichloro-1H-benzoimidazol-2-yl)-2,2,2-trifluoro-ethanol (91.0 g, 0.32 mol), 4-methoxy-TEMPO (14.3 g, 0.077 mol), and KBr (4 g, 0.0336 mol) in THF (900 mL). The brown homogenous solution was stirred for 15 min while cooling to −10° C. After cooling, NaOCl (670 ml) was added dropwise over a ½h period. The reaction mixture was diluted with EtOAc (1.5 L) and $H_2O$ (1.5 L). When the effervescence ceased, the phases were split and the aqueous layer was back extracted with EtOAc (2 L). The combined organic layer was washed with brine (2 L); dried over $Na_2SO_4$, filtered and evaporated to dryness to yield a crude residue. The crude residue was purified by flash chromatography using $SiO_2$ (1 kg) and 40% EtOAc/hexanes (24 L) and the product dried in vacuo for 18 h at 50° C. to yield 1-(5,6-dichloro-1H-benzoimidazol-2-yl)-2,2,2-trifluoro-ethanone as a yellow solid.

Example 3

2-(5,6-Dichloro-1H-benzoimidazol-2-yl)-1,1,1-trifluoro-pent-4-en-2-ol (#1)

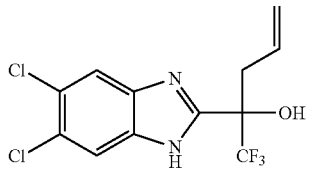 [SMILES: C=CCC(O)(c1nc2cc(Cl)c(Cl)cc2[nH]1)C(F)(F)F]

1-(5,6-Dichloro-1H-benzoimidazol-2-yl)-2,2,2-trifluoro-ethanone (1.41 g; 4.99 mmol), allyl bromide (0.85 mL; 10.05 mmol) and indium (1.15 g; 10.05 mmol) were suspended in THF (50 mL) and 0.01M HCl (150 mL) and stirred vigorously over 18 hours. The layers were separated and the aqueous layer was extracted with ethyl acetate (3×30 mL). The combined extracts were washed with brine (50 mL) and dried over $Na_2SO_4$. The resulting crude brown oil was purified by column chromatography ($SiO_2$; 20% ethyl acetate/hexanes) to yield the title compound as a tan solid.

$^1$H NMR (400 MHz, $CD_3CN$): δ 7.79 (s, 2H), δ 5.59 (m, 1H), δ 5.17 (d, J=17.1 Hz, 1H), δ 5.07 (d, J=11 Hz, 1H), δ 3.13 (dd, J=6.8, 14.3 Hz, 1H), δ 2.88 (dd, J=7.2, 14.3 Hz, 1H)

MS calculated for $C_{12}H_9Cl_2F_3N_2O$: 325.11

MS measured: 325, 327 (M+H); 323, 325 (M−1).

(+)-Enantiomer of 2-(5,6-Dichloro-1H-benzoimidazol-2-yl)-1,1,1-trifluoro-pent-4-en-2-ol (#23) and (−)-Enantiomer of 2-(5,6-Dichloro-1H-benzoimidazol-2-yl)-1,1,1-trifluoro-pent-4-en-2-ol (#24)

A portion of the product prepared according to the procedure described above was dissolved in 20% isopropanol/hexane and chromatographed using a ChiralPak AD 5×50 cm column (70 mL/min flow rate, mobile phase 10% isopropanol/hexane) with the (+)-enantiomer (#23) eluting first followed by the (−) enantiomer (#24). $^1$H NMR and Mass Spectral data for the two isolated compounds was identical to of Compound #1 isolated above.

Example 4

2-(5,6-Dichloro-1H-benzoimidazol-2-yl)-1,1,1-trifluoro-penta-3,4-dien-2-ol (#3) and 2-(5,6-Dichloro-1H-benzoimidazol-2-yl)-1,1,1-trifluoro-pent-4-yn-2-ol (#2)

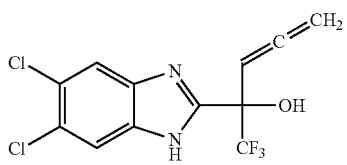 and 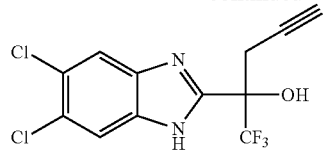

1-(5,6-Dichloro-1H-benzoimidazol-2-yl)-2,2,2-trifluoro-ethanone (1.42 g; 5.03 mmol), propargyl bromide (80% in toluene; 1.10 mL; 15.4 mmol) and indium (1.56 g; 13.6 mmol) were suspended in THF (50 mL) and 0.01M HCl (150 mL) and stirred vigorously over 18 hours. The layers were separated and the aqueous layer was extracted with ethyl acetate (3×30 mL). The combined extracts were washed with brine (50 mL) and dried over $Na_2SO_4$. The resulting crude brown oil was a mixture of 2-(5,6-dichloro-1H-benzoimidazol-2-yl)-1,1,1-trifluoro-penta-3,4-dien-2-ol and 2-(5,6-dichloro-1H-benzoimidazol-2-yl)-1,1,1-trifluoro-pent-4-yn-2-ol that was purified by column chromatography ($SiO_2$; 20% ethyl acetate/hexanes).

2-(5,6-Dichloro-1H-benzoimidazol-2-yl)-1,1,1-trifluoro-penta-3,4-dien-2-ol was isolated as a light yellow solid $^1$H NMR (300 MHz, $CD_3CN$): δ 7.82 (s, 2H), δ 5.93 (t, J=6.7 Hz, 1H), δ 5.16 (d, J=6.6 Hz, 1H)

MS calculated for $C_{12}H_7Cl_2F_3N_2O$: 323.10

MS measured: 323, 325 (M+H); 321, 323 (M−1).

2-(5,6-dichloro-1H-benzoimidazol-2-yl)-1,1,1-trifluoro-pent-4-yn-2-ol was isolated as an orange-yellow solid $^1$H NMR (400 MHz, $CD_3CN$): δ 7.82 (s, 2H), δ 3.35 (dd, J=2.6, 16.8 Hz, 1H), δ 3.11 (dd, J=2.6, 17.0 Hz, 1H), δ 5.59 (m, 1H), δ 2.18 (s, 1H)

MS calculated for $C_{12}H_7Cl_2F_3N_2O$: 323.10

MDS measured: 323, 325 (M+H); 321, 323 (M−1).

(+)-Enantiomer of 2-(5,6-Dichloro-1H-benzoimidazol-2-yl)-1,1,1-trifluoro-penta-3,4-dien-2-ol (#31) and (−)-Enantiomer of 2-(5,6-Dichloro-1H-benzoimidazol-2-yl)-1,1,1-trifluoro-penta-3,4-dien-2-ol (#32)

A portion of the isolated Compound #2 product prepared according to the procedure described above was dissolved in 20% ethanol/heptane and chromatographed using a ChiralPak AD 5×50 cm column (70 mL/min flow rate, mobile phase 20% ethanol/heptane) with the (+)-enantiomer (#31) eluting first followed by the (−) enantiomer (#32). $^1$H NMR and Mass Spectral data for the two isolated compounds was identical to of Compound #2 isolated above.

Example 5

2-(5,6-Dichloro-1H-benzoimidazol-2-yl)-1,1,1-trifluoro-but-3-en-2-ol (#4)

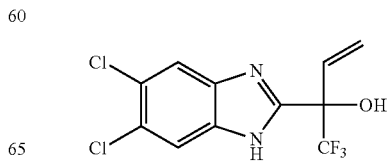

To 1-(5,6-dichloro-1H-benzoimidazol-2-yl)-2,2,2-trifluoro-ethanone (326 mg) in THF (10 mL) –78° C. was added vinyl magnesium bromide (2.42 mL of 1.0 M in THF) dropwise. The resulting mixture was then stirred at 0° C. for 2 hr. The resulting mixture was quenched with H$_2$O and 1N HCl, extracted with EtOAc, dried over Na$_2$SO$_4$, filtered, and concentrated to yield a residue. The residue was purified by flash chromatography with Biotage 40s+ column and elution with 10%-40% EtOAc/hexanes to yield a yellow gum. The yellow gum was dissolved in a minimal amount of CH$_2$Cl$_2$ and triturated with hexanes to yield the title compound as a light yellow solid.

$^1$H NMR (300 MHz, d$_6$-DMSO): δ 13.03 (br s, 1H), 7.99 (s, 1H), 7.76 (s, 1H), 7.69 (s, 1H), 6.54 (dd, 1H, J=10.8, 17.2 Hz), 5.71 (d, 1H, J=17.2 Hz), 5.59 (d, 1H, J=10.8 Hz)

MS (M−1)=309.

Example 6

2-(5,6-Dichloro-1H-benzoimidazol-2-yl)-1,1,1-trifluoro-3-methyl-pent-3,4-dien-2-ol (#6)

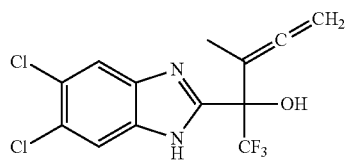 [SMILES: C=C=C(C)C(O)(c1nc2cc(Cl)c(Cl)cc2[nH]1)C(F)(F)F]

1-(5,6-Dichloro-1H-benzoimidazol-2-yl)-2,2,2-trifluoro-ethanone (0.61 g; 2.2 mmol), 1-bromo-2-butyne (1.7 mL; 18.8 mmol) and indium (2.49 g; 21.7 mmol) were suspended in THF (10 mL) and 0.045 M HCl (20 mL) and stirred vigorously overnight. The reaction mixture was diluted with water (60 mL) and ethyl acetate (40 mL), the layers were separated and the aqueous layer was extracted with ethyl acetate (3×20 mL). The combined extracts were washed with brine (50 mL) and dried over Na$_2$SO$_4$. The resulting crude material was purified by column chromatography (SiO$_2$; 20% ethyl acetate/hexanes) to yield the title compound as an off-white solid.

$^1$H NMR (400 MHz, CDCl$_3$): δ 7.76 (s, 2H), δ 5.08 (m, 2H), δ 1.88 (s, 3H)

MS calculated for C$_{13}$H$_9$Cl$_2$F$_3$N$_2$O: 337.12
MS measured: 337, 339 (M+H); 335, 337 (M−1).

Compound #33 (also known as 2-(5,6-dichloro-1H-benzoimidazol-2-yl)-1,1,1-trifluoro-hex-4-yn-2-ol) was prepared as a minor by-product of the above described reaction and isolated as a residue.

Example 7

3-(5,6-Dichloro-1H-benzoimidazol-2-yl)-4,4,4-trifluoro-3-hydroxy-butyronitrile (#7)

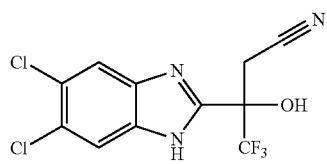 [SMILES: N#CCC(O)(c1nc2cc(Cl)c(Cl)cc2[nH]1)C(F)(F)F]

To a solution of dry acetonitrile (0.4 mL) in THF (10 mL) at −78° C. was added n-BuLi (2.9 mL of 2.5 M in hexanes). The resulting mixture was stirred for 45 min. at −78° C. To the solution was then added a solution of 1-(5,6-dichloro-1H-benzoimidazol-2-yl)-2,2,2-trifluoro-ethanone (930 mg) in THF (5 mL). The resulting mixture was stirred at −78° C. for 1 hr. The reaction was quenched with NH$_4$Cl (aq) and the resulting mixture extracted with EtOAc. The combined extracts were washed with brine and dried over Na$_2$SO$_4$. The resulting crude material was purified by column chromatography (SiO$_2$; 0-15% ethyl acetate/hexanes) to yield the title compound as a yellow solid.

$^1$H NMR (300 MHz, d$_6$-DMSO): δ 13.31 (br, 1H), 8.48 (s, 1H), 8.04 (s, 1H), 7.73 (s, 1H), 3.59 (ABq, 2H, J$_{AB}$=16.9 Hz, Δv$_{AB}$=59 Hz).

Example 8

2-(5,6-Dichloro-1H-benzoimidazol-2-yl)-1,1,1-trifluoro-pent-3-yn-2-ol (#8)

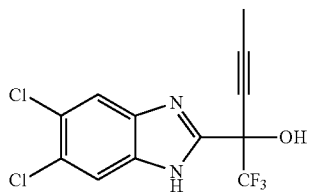 [SMILES: CC#CC(O)(c1nc2cc(Cl)c(Cl)cc2[nH]1)C(F)(F)F]

To 1-(5,6-dichloro-1H-benzoimidazol-2-yl)-2,2,2-trifluoro-ethanone (535 mg) in THF (10 mL) at −78° C. was added 1-propynyl magnesium bromide (8 mL of 0.5 M in THF) dropwise. The resulting mixture was then stirred at 0° C. for 3 hr. The reaction was quenched with H$_2$O and 1N HCl, extracted with EtOAc, dried over Na$_2$SO$_4$, filtered, and concentrated to yield a residue. The residue was purified by flash chromatography with Biotage 40s+ column and elution with 10%-40% EtOAc/hexanes to yield a yellow solid. The yellow solid was dissolved in a minimal amount of CH$_2$Cl$_2$ and triturated with hexanes to yield the title compound as a white solid.

$^1$H NMR (300 MHz, d$_6$-DMSO): δ 13.10 (br s, 1H), 8.48 (s, 1H), 8.01 (s, 1H), 7.69 (s, 1H), 1.97 (s, 3H).

MS (M−1)=321.1

Example 9

2-(5,6-Dichloro-1H-benzoimidazol-2-yl)-1,1,1-trifluoro-3-methyl-but-3-en-2-ol (#9)

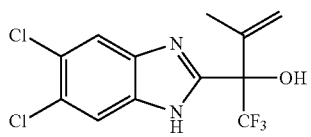 [SMILES: C=C(C)C(O)(c1nc2cc(Cl)c(Cl)cc2[nH]1)C(F)(F)F]

To 1-(5,6-dichloro-1H-benzoimidazol-2-yl)-2,2,2-trifluoro-ethanone (793 mg) in THF (5 mL) at −78° C. was added isopropenyl magnesium bromide (12.3 mL of 0.5 M in THF) dropwise. The resulting mixture was then stirred at 0° C. for 5 hr. The reaction was quenched with H$_2$O and 1N HCl, extracted with EtOAc, dried over Na$_2$SO$_4$, filtered, and concentrated to a residue. The residue was purified by flash chromatography with Biotage 40s+ column and elution with 10%-40% EtOAc/hexanes to yield an orange gum. The orange gum was dissolved in a minimal amount of $CH_2Cl_2$ and triturated with hexanes to yield the title compound as a peach-colored solid.

$^1$H NMR (400 MHz, $d_4$-MeOD): δ 7.75 (br, 2H), 5.42 (s, 1H), 5.31 (s, 1H), 1.81 (s, 3H), NH and OH protons were not observed.

Example 10

1-(5,6-Dichloro-1H-benzoimidazol-2-yl)-2,2,2-trifluoro-1-phenyl-ethanol (#10)

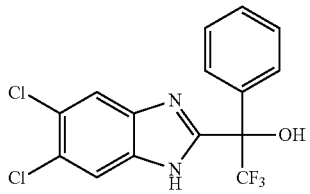 [SMILES: OC(c1ccccc1)(c1nc2cc(Cl)c(Cl)cc2[nH]1)C(F)(F)F]

To 1-(5,6-dichloro-1H-benzoimidazol-2-yl)-2,2,2-trifluoro-ethanone (595 mg) in THF (5 mL) at −78° C. was added phenyl magnesium bromide (4.6 mL of 1M in THF) dropwise. The resulting mixture was stirred at 0° C. for 4 hr. The reaction was quenched with $H_2O$ and 1N HCl, extracted with EtOAc, dried over $Na_2SO_4$, filtered, and concentrated to a residue. The residue was purified by flash chromatography with Biotage 40s+ column and elution with 10%-40% EtOAc/hexanes to yield a yellow solid. The yellow solid was dissolved in a minimal amount of $CH_2Cl_2$ and triturated with hexanes to yield the title compound as a tan solid.

MS calculated for $C_{15}H_9Cl_2F_3N_2O$: 360.00. found: 361 (M+1).

Example 11

2-(5,6-Dichloro-1H-benzoimidazol-2-yl)-1,1,1-trifluoro-4-methyl-pent-4-en-2-ol (#13)

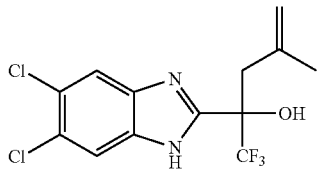 [SMILES: C=C(C)CC(O)(c1nc2cc(Cl)c(Cl)cc2[nH]1)C(F)(F)F]

To 1-(5,6-dichloro-1H-benzoimidazol-2-yl)-2,2,2-trifluoro-ethanone (609 mg) in THF (4 mL) and $H_2O$ (12 mL) at room temperature were added 3-bromo-2-methyl-propene (0.31 mL), followed by indium powder (279 mg, −100 mesh). The resulting mixture was then stirred at room temperature for 18 hr. The resulting mixture was filtered through a pad of Celite®, rinsed with EtOAc, the layers separated, the aqueous layer extracted with EtOAc, dried over $Na_2SO_4$, filtered, and concentrated to yield a residue. The residue was purified by flash chromatography with Biotage 40s+ column and elution with 10%-40% EtOAc/hexanes to yield an orange gum. The orange gum was dissolved in a minimal amount of $CH_2Cl_2$ and triturated with hexanes to yield the title compound as an orange solid.

$^1$H NMR (400 MHz, $d_4$-MeOD): δ 7.78 (br, 1H), 7.69 (br, 1H), 4.73 (s, 1H), 4.69 (s, 1H), 2.98 (ABq, 2H, $J_{AB}$=14.3 Hz, $\Delta v_{AB}$=120.4 Hz), 1.54 (s, 3H), NH and OH protons were not observed.

Example 12

2-(5,6-Dichloro-1H-benzoimidazol-2-yl)-1,1,1-trifluoro-4-methyl-pent-3-en-2-ol (#14)

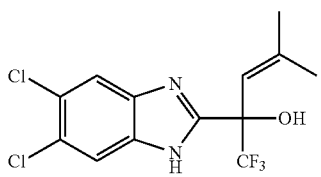 [SMILES: CC(C)=CC(O)(c1nc2cc(Cl)c(Cl)cc2[nH]1)C(F)(F)F]

To 1-(5,6-dichloro-1H-benzoimidazol-2-yl)-2,2,2-trifluoro-ethanone (565 mg) in THF (5 mL) at 0° C. was added Grignard reagent, which was freshly prepared from 1-bromo-2-methyl-propene (0.51 mL), a small iodine flake, and magnesium powder (146 mg) in THF (5 mL). The resulting mixture was then stirred at room temperature for 3 hr. The reaction was quenched with $NH_4Cl$ (sat. aq), filtered through a pad of Celite®, rinsed with EtOAc, the layers were separated, the aqueous layer extracted with EtOAc, dried over $Na_2SO_4$, filtered, and concentrated to yield a residue. The residue was purified by flash chromatography with Biotage 40s+ column and elution with 10%-40% EtOAc/hexanes to yield a yellow solid. The yellow solid was dissolved in a minimal amount of $CH_2Cl_2$ and triturated with hexanes to yield the title compound as a yellow solid.

$^1$H NMR (400 MHz, $d_4$-MeOD): δ 7.73 (br, 2H), 5.91 (s, 1H), 1.84 (s, 3H), 1.46 (s, 3H), NH and OH protons were not observed.

MS (M+1)=339.0

Example 13

2-(5,6-Dichloro-1H-benzoimidazol-2-yl)-1,1,1-trifluoro-cis-pent-3-en-2-ol (#15)

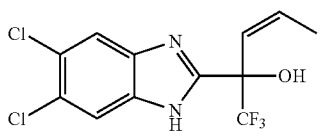 [SMILES: C/C=C\C(O)(c1nc2cc(Cl)c(Cl)cc2[nH]1)C(F)(F)F]

To 1-(5,6-dichloro-1H-benzoimidazol-2-yl)-2,2,2-trifluoro-ethanone (510 mg) in THF (5 mL) at 0° C. was added Grignard reagent, which was freshly prepared from cis-1-bromo-1-propene (1.07 mL), a small iodine flake, and magnesium powder (306 mg) in THF (5 mL). The resulting mixture was then stirred at room temperature for 3 hr. The reaction was quenched with $NH_4Cl$ (sat. aq), filtered through a pad of Celite®, rinsed with EtOAc, the layers were separated, the aqueous layer extracted with EtOAc, dried over $Na_2SO_4$, filtered, and concentrated to yield a residue. The residue was purified by flash chromatography with Biotage 40s+ column and elution with 10%-40% EtOAc/hexanes to yield a yellow solid. The yellow solid was dissolved in a minimal amount of $CH_2Cl_2$ and triturated with hexanes to yield the title compound as a yellow solid.

$^1$H NMR (400 MHz, $d_4$-MeOD): δ 7.77 (br, 1H), 7.72 (br, 1H), 6.07-6.12 (m, 1H), 6.01-6.05 (m, 1H), 1.52 (dd, 3H, J=1.2, 6.9 Hz), NH and OH protons were not observed.

MS (M+1)=325.1

Example 14

2-(5,6-Dichloro-1H-benzoimidazol-2-yl)-1,1,1-trifluoro-trans-pent-3-en-2-ol (#16)

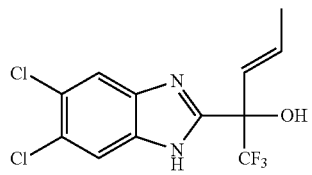 [SMILES: C/C=C/C(O)(c1nc2cc(Cl)c(Cl)cc2[nH]1)C(F)(F)F]

To 1-(5,6-dichloro-1H-benzoimidazol-2-yl)-2,2,2-trifluoro-ethanone (636 mg) in THF (5 mL) at 0° C. was added Grignard reagent, which was freshly prepared from trans-1-bromo-1-propene (1.35 mL), a small iodine flake, and magnesium powder (382 mg) in THF (5 mL). The resulting mixture was then stirred at room temperature for 3 hr. The reaction was quenched with $NH_4Cl$ (sat. aq), filtered through a pad of Celite®, rinsed with EtOAc, the layers were separated, the aqueous layer extracted with EtOAc, dried over $Na_2SO_4$, filtered, and concentrated to yield a residue. The residue was purified by flash chromatography with Biotage 40s+ column and elution with 10%-40% EtOAc/hexanes to yield a yellow solid. The yellow solid was dissolved in a minimal amount of $CH_2Cl_2$ and triturated with hexanes to yield the title compound as a yellow solid.

$^1$H NMR (400 MHz, $d_4$-MeOD): δ 7.79 (br, 1H), 7.71 (br, 1H), 6.13 (s, 1H), 6.11-6.13 (m, 1H), 1.82 (apparent d, 3H, J=4.9 Hz), NH and OH protons were not observed

MS (M+1)=325.1.

Example 15

4-(5,6-Dichloro-1H-benzoimidazol-2-yl)-5,5,5-trifluoro-pent-2-yne-1,4-diol (#17)

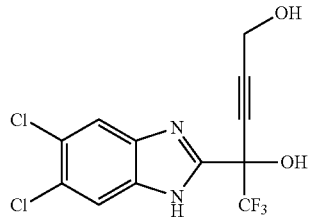 [SMILES: OCC#CC(O)(c1nc2cc(Cl)c(Cl)cc2[nH]1)C(F)(F)F]

To 1-(5,6-dichloro-1H-benzoimidazol-2-yl)-2,2,2-trifluoro-ethanone (3.2 g) in THF (40 mL) at 0° C. was added lithium reagent which was freshly prepared from tetrahydropyran-2-propynyloxy (1.6 mL) and n-BuLi (4.5 mL of 2.5 M in hexanes) in THF (20 mL) (stirred at −78° C. for 2 h). The resulting mixture was then stirred at room temperature for 3 hr. The reaction was quenched with $NH_4Cl$ (sat. aq), filtered through a pad of Celite®, rinsed with EtOAc, the layer were separated, the aqueous later extracted with EtOAc, dried over $Na_2SO_4$, filtered, and concentrated to yield a residue. The residue was purified by flash chromatography with Biotage 40 m+ column and elution with 5%-30% EtOAc/hexanes to an orange solid.

To a solution of THP ether (2.28 g, see procedure above) in methanol (25 mL) was added p-toluenesulfonic acid monohydrate (2.05 g) and the resulting mixture stirred at room temperature for 2 h. The reaction mixture was then quenched with $Na_2CO_3$ (aq), extracted with EtOAc, and dried over $Na_2SO_4$ to yield a residue. The residue was purified by flash chromatography with Biotage 40s+ column and elution with 5%-35% EtOAc/hexanes to yield the title compound as an orange solid.

$^1$H NMR (300 MHz, $d_6$-DMSO): δ 13.16 (br, 1H), 8.66 (br, 1H), 8.01 (s, 1H), 7.69 (s, 1H), 5.46 (t, 1H, J=6.1 Hz), 4.23 (d, 2H, J=6.0 Hz)

MS (M+1)=339.

Example 16

2-(5,6-Dichloro-1H-benzoimidazol-2-yl)-1,1,1-trifluoro-3,3-dimethyl-pent-4-en-2-ol (#25)

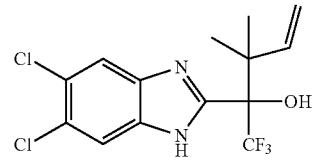 [SMILES: C=CC(C)(C)C(O)(c1nc2cc(Cl)c(Cl)cc2[nH]1)C(F)(F)F]

1-(5,6-Dichloro-1H-benzoimidazol-2-yl)-2,2,2-trifluoroethanone (0.31 g; 1.09 mmol), 3,3-dimethylallyl bromide (90%; 1.40 mL; 10.8 mmol) and indium (1.26 g; 11.0 mmol) were suspended in THF (10 mL) and 0.02 M HCl (15 mL) and stirred vigorously over 18 hours. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude oil. The crude oil was purified by column chromatography ($SiO_2$; 20% ethyl acetate/hexanes) to yield the title compound as an off-white solid.

$^1$H NMR (400 MHz, $CD_3CN$): δ 7.88 (s, 2H), 6.18 (dd, 1H, J=1.3, 10.9 Hz), 5.14 (m, 2H), 1.19 (s, 3H), 1.17 (s, 3H)

MS calculated for $C_{14}H_{13}Cl_2F_3N_2O$: 353.17
MS measured: 353, 355 (M+H); 351, 353 (M−1).

Example 17

2-(5,6-Dichloro-1H-benzoimidazol-2-yl)-1,1,1-trifluoro-3-methyl-pent-4-en-2-ol (#26)

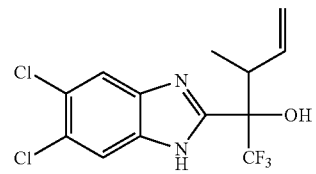 [SMILES: C=CC(C)C(O)(c1nc2cc(Cl)c(Cl)cc2[nH]1)C(F)(F)F]

1-(5,6-Dichloro-1H-benzoimidazol-2-yl)-2,2,2-trifluoro-ethanone (0.31 g; 1.09 mmol), crotyl bromide (1.2 mL; 11.8 mmol) and indium (1.26 g; 11.0 mmol) were suspended in THF (10 mL) and 0.02 M HCl (15 mL) and stirred vigorously over 18 hours. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude oil. The crude oil was purified by column chromatography ($SiO_2$; 20% ethyl acetate/hexanes) to yield the title compound as a 2:1 mixture of diastereomers as an off-white solid.

$^1$H NMR (400 MHz, $CD_3CN$): δ 7.88 (s, 2H), (Mixture of diastereomers) δ 5.92 and δ 5.78 (m, 1H), (Mixture of diastereomers) δ 5.26 and δ 4.99 (d, J=17.1 Hz, 1H), (Mixture of diastereomers) δ 5.17 and δ 4.92 (d, J=10.3 Hz, 1H), (Mixture of diastereomers) δ 3.26 and δ 3.18 (m, 1H), (Mixture of diastereomers) δ 1.16 and δ 0.86 (d, J=6.9 Hz, 3H)

MS calculated for $C_{13}H_{11}Cl_2F_3N_2O$: 339.14
MS measured: 339, 341 (M+H); 337, 339 (M−1)

Example 18

2-[2-(5,6-Dichloro-1H-benzoimidazol-2-yl)-3,3,3-trifluoro-2-hydroxy-propyl]-acrylic acid (#27)

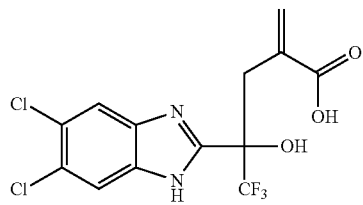 [SMILES: C=C(CC(O)(c1nc2cc(Cl)c(Cl)cc2[nH]1)C(F)(F)F)C(=O)O]

1-(5,6-Dichloro-1H-benzoimidazol-2-yl)-2,2,2-trifluoro-ethanone (0.30 g; 1.05 mmol), 2-(bromomethyl)acrylic acid (1.80 g; 10.9 mmol) and indium (1.23 g; 10.7 mmol) were suspended in THF (10 mL) and 0.02 M HCl (15 mL) and stirred vigorously over 18 hours. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude material. The crude material was purified by column chromatography ($SiO_2$; 50% ethyl acetate/hexanes) to yield the title compound as an off-white solid.

$^1$H NMR (400 MHz, $CD_3CN$): δ 7.78 (s, 2H), 6.16 (s, 1H), 5.69 (s, 1H), 3.75 (d, J=10.4 Hz, 1H), 3.67 (d, J=10.3 Hz, 1H)

MS calculated for $C_{13}H_9Cl_2F_3N_2O_3$: 369.12
MS measured: 369, 371 (M+H); 367, 369 (M−1).

Example 19

2-(5,6-Dichloro-1H-benzoimidazol-2-yl)-1,1,1-trifluoro-3-phenyl-pent-4-en-2-ol (#28)

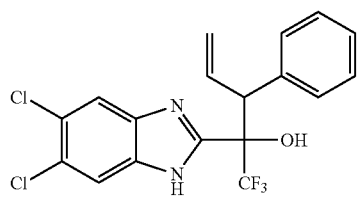 [SMILES: C=CC(c1ccccc1)C(O)(c1nc2cc(Cl)c(Cl)cc2[nH]1)C(F)(F)F]

1-(5,6-Dichloro-1H-benzoimidazol-2-yl)-2,2,2-trifluoro-ethanone (0.30 g; 1.04 mmol), cinnamyl bromide (1.6 mL; 10.5 mmol) and indium (1.22 g; 10.7 mmol) were suspended in THF (10 mL) and 0.02 M HCl (15 mL) and stirred vigorously over 18 hours. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude oil. The crude oil was purified by column chromatography ($SiO_2$; 20% ethyl acetate/hexanes) to yield the title compound as an off-white solid.

$^1$H NMR (400 MHz, $CD_3CN$): δ 10.63 (br s, 1H), 7.77 (s, 1H), 7.55 (s, 1H), 7.14 (m, 2H), 7.06 (m, 3H), 6.47 (dd, J=10.0, 18.7 Hz, 1H), 5.32 (m, 2H), 5.24 (dd, J=1.5, 10.2 Hz, 1H), 4.35 (d, J=9.9 Hz, 1H)

MS calculated for $C_{18}H_{13}Cl_2F_3N_2O$: 401.21
MS measured: 401, 403 (M+H); 399, 401 (M−1).

Example 20

2-(5,6-Dichloro-1H-benzoimidazol-2-yl)-1,1,1-trifluoro-5-phenyl-pent-4-yn-2-ol #34

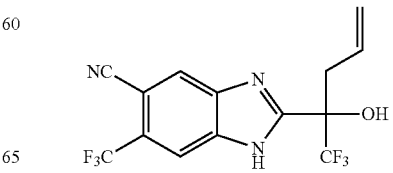

2-(5,6-Dichloro-1H-benzoimidazol-2-yl)-1,1,1-trifluoro-pent-4-yn-2-ol (0.27 g; 0.83 mmol), iodobenzene (0.14 mL; 1.3 mmol), dichlorobis(triphenylphosphine)palladium (31.7 mg; 0.045 mmol), copper iodide (17.8 mg; 0.093 mmol) and triethylamine (0.25 mL; 1.8 mmol) were suspended in THF (5 mL) and the resulting mixture stirred vigorously overnight. The reaction mixture was then concentrated in vacuo and the resulting crude brown oil was purified by column chromatography ($SiO_2$; 50% ether/$CH_2Cl_2$) to yield the title compound as an orange-yellow solid.

$^1$H NMR (400 MHz, $CD_3CN$): δ 7.90 (s, 1H), 7.75 (s, 1H), 7.29 (m, 3H), 7.21 (m, 2H), 3.54 (d, J=17.1 Hz, 1H), 3.33 (d, J=17.1 Hz, 1H)

MS calculated for $C_{18}H_{11}Cl_2F_3N_2O$: 399.19
MS measured: 399, 401 (M+H); 397, 399 (M−1).

Example 21

2-(1-Hydroxy-1-trifluoromethyl-but-3-enyl)-6-trifluoromethyl-1H-benzoimidazole-5-carbonitrile (#38)

2-(2,2,2-Trifluoro-acetyl)-6-trifluoromethyl-1H-benzoimidazole-5-carbonitrile (0.31 g; 0.95 mmol), allyl bromide (0.82 mL; 9.5 mmol) and indium (1.09 g; 9.5 mmol) were suspended in THF (12 mL) and 0.03 M HCl (10 mL) and stirred vigorously overnight. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude material. The crude material was purified by column chromatography ($SiO_2$; 20% ethyl acetate/hexanes) to yield the title compound as an off-white solid.

$^1$H NMR (400 MHz, $CD_3CN$): δ 8.25 (s, 1H), 8.12 (s, 1H), 5.58 (m, 1H), 5.17 (m, 1H), 5.07 (m, 1H), 3.17 (dd, J=7.1, 14.3 Hz, 1H), 2.93 (dd, J=7.2, 14.3 Hz, 1H)

MS calculated for $C_{14}H_9F_6N_3O$: 349.23
MS measured: 350 (M+H); 348 (M−1).

Example 22

2-(1-Hydroxy-1-trifluoromethyl-but-3-ynyl)-6-trifluoromethyl-1H-benzoimidazole-5-carbonitrile (#39)

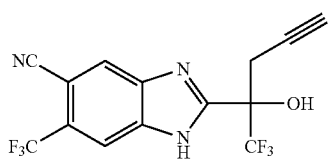 [SMILES: C#CCC(O)(c1nc2cc(C#N)c(C(F)(F)F)cc2[nH]1)C(F)(F)F]

2-(2,2,2-Trifluoro-acetyl)-6-trifluoromethyl-1H-benzoimidazole-5-carbonitrile (0.31 g; 0.94 mmol), propargyl bromide (80% in toluene; 1.1 mL; 12.3 mmol) and indium (1.08 g; 9.5 mmol) were suspended in THF (12 mL) and 0.03 M HCl (10 mL) and stirred vigorously overnight. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude material. The crude material was purified by column chromatography ($SiO_2$; 20% ethyl acetate/hexanes) to yield the title compound as an off-white solid.

$^1$H NMR (400 MHz, $CD_3CN$): δ 8.29 (s, 1H), δ 8.15 (s, 1H), 3.39 (dd, J=2.6, 17.1 Hz, 1H), 3.15 (dd, J=2.7, 17.1 Hz, 1H), 2.20 (t, J=2.7 Hz, 1H)

MS calculated for $C_{14}H_7F_6N_3O$: 347.22
MS measured: 348 (M+H); 346 (M−1)

Example 23

2-(5,6-Dichloro-1H-benzoimidazol-2-yl)-1,1,1-trifluoro-hex-5-en-2-ol (#40)

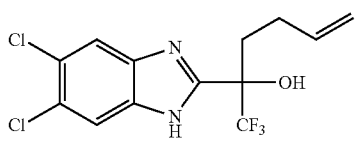 [SMILES: C=CCCC(O)(c1nc2cc(Cl)c(Cl)cc2[nH]1)C(F)(F)F]

To 1-(5,6-dichloro-1H-benzoimidazol-2-yl)-2,2,2-trifluoro-ethanone (595 mg) in THF (3 mL) at −78° C. was added 3-butenyl magnesium bromide (7.8 mL of 0.5 M in THF) dropwise. The resulting mixture was then stirred at 0° C. for 4 hr. The reaction was quenched with $H_2O$ and 1N HCl, extracted with EtOAc, dried over $Na_2SO_4$, filtered, and concentrated to yield a residue. The residue was purified by flash chromatography with Biotage 40s+ column and elution with 10%-40% EtOAc/hexanes to yield a yellow solid. The yellow solid was dissolved in a minimal amount of $Et_2O$ and triturated with hexanes to yield the title compound as a tan solid.

$^1$H NMR (300 MHz, $d_6$-DMSO): δ 12.95 (br s, 1H), 7.94 (s, 1H), 7.73 (s, 1H), 7.41 (s, 1H), 5.53-5.81 (m, 1H), 4.89-5.00 (m, 2H), 2.36-2.44 (m, 1H), 1.99-2.23 (m, 2H), 1.62-1.72 (m, 1H)

MS (M+1)=339.0

Example 24

2-(1-Hydroxy-2-methyl-1-trifluoromethyl-buta-2,3-dienyl)-6-trifluoromethyl-1H-benzoimidazole-5-carbonitrile (#41)

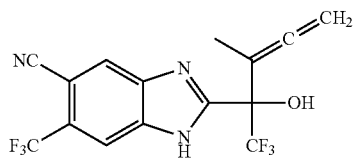 [SMILES: C=C=C(C)C(O)(c1nc2cc(C#N)c(C(F)(F)F)cc2[nH]1)C(F)(F)F]

2-(2,2,2-Trifluoro-acetyl)-6-trifluoromethyl-1H-benzoimidazole-5-carbonitrile (0.31 g; 0.94 mmol), 1-bromo-2-butyne (0.85 mL; 9.4 mmol) and indium (1.09 g; 9.5 mmol) were suspended in THF (12 mL) and 0.03 M HCl (10 mL) and stirred vigorously overnight. The reaction mixture was then diluted with water (60 mL) and ethyl acetate (40 mL), the layers were separated and the aqueous layer was extracted with ethyl acetate (3×20 mL). The combined extracts were washed with brine (50 mL) and dried over $Na_2SO_4$ to yield a crude material. The crude material was purified by column chromatography ($SiO_2$; 20% ethyl acetate/hexanes) to yield the title compound as a white solid.

$^1$H NMR (400 MHz, $CD_3CN$): δ 8.27 (s, 1H), 8.13 (s, 1H), 5.00 (dd, J=3.1, 6.2 Hz, 1H), 1.71 (s, 3H)

MS calculated for $C_{15}H_9F_6N_3O$: 361.24
MS measured: 362 (M+H); 360 (M−1)

Example 25

2-(5,6-Dichloro-1H-benzoimidazol-2-yl)-1,1,1-trifluoro-3,4-dimethyl-pent-3-en-2-ol #42

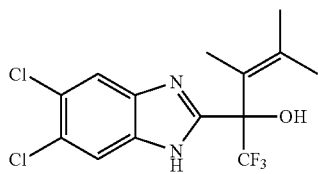 [SMILES: CC(C)=C(C)C(O)(c1nc2cc(Cl)c(Cl)cc2[nH]1)C(F)(F)F]

To 1-(5,6-dichloro-1H-benzoimidazol-2-yl)-2,2,2-trifluoro-ethanone (577 mg) in THF (5 mL) at 0° C. was added Grignard reagent, which was freshly prepared from 2-bromo-3-methyl-2-butene (1.73 mL), a small iodine flake, and magnesium powder (347 mg) in THF (5 mL). The resulting mixture was stirred at room temperature for 3 hr. The reaction was quenched with NH₄Cl (sat. aq), filtered through a pad of Celite®, rinsed with EtOAc, the layers were separated, the aqueous layer extracted with EtOAc, dried over Na₂SO₄, filtered, and concentrated to yield a residue. The residue was purified by flash chromatography with Biotage 40s+ column and elution with 10%-40% EtOAc/hexanes to yield a yellow solid. The yellow solid was dissolved in a minimal amount of CH₂Cl₂ and triturated with hexanes to yield the title compound as an off-white solid.

¹H NMR (400 MHz, d₄-MeOD): δ 7.78 (s, 1H), 7.66 (s, 1H), 1.97 (s, 3H), 1.77 (s, 3H), 1.34 (s, 3H), NH and OH protons were not observed.

MS (M+1)=353.0

Example 26

(+)-2-(5,6-dichloro-1H-benzoimidazol-2-yl)-1,1,1-trifluoro-but-3-en-2-ol (#43) and (−)-2-(5,6-dichloro-1H-benzoimidazol-2-O-1,1,1-trifluoro-but-3-en-2-ol (#44)

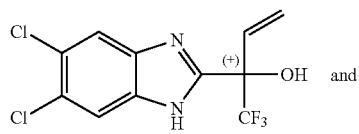

and

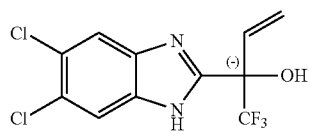

2-(5,6-Dichloro-1H-benzoimidazol-2-yl)-1,1,1-trifluoro-but-3-en-2-ol product (285 mg) was then separated into the (+) and (−) enantiomers via HPLC on Chiralpak AD (5×50 cm), using 7% isopropanol in heptane as the eluent (70 mL/min).

¹H NMR (300 MHz, d₆-DMSO): δ 13.03 (br s, 1H), 7.99 (s, 1H), 7.76 (s, 1H), 7.69 (s, 1H), 6.54 (dd, 1H, J=10.8, 17.2 Hz), 5.71 (d, 1H, J=17.2 Hz), 5.59 (d, 1H, J=10.8 Hz)

MS (M−1)=309.

(+)-2-(5,6-dichloro-1H-benzoimidazol-2-yl)-1,1,1-trifluoro-but-3-en-2-ol (#43)

[α]CHCl₃=+105 (c=0.5 g/100 mL)

(−)-2-(5,6-dichloro-1H-benzoimidazol-2-yl)-1,1,1-trifluoro-but-3-en-2-ol (#44)

[α]CHCl₃=−108 (c=0.5 g/100 mL)

Example 27

2-Hydroxy-2-trifluoromethyl-but-3-enoic acid ethyl ester

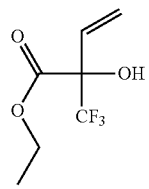

To a solution of ethyl 3,3,3-trifluoropyruvate (14.2 g) in THF (200 mL) at −78° C. was added vinyl magnesium bromide (84 mL of 1M in THF) dropwise via addition funnel. The resulting mixture was then warmed to ambient temperature over 2 h. The reaction was quenched by pouring the mixture over ice. To the resulting mixture was then added 2 N HCl, the mixture was extracted with EtOAc, and dried over Na₂SO₄. After concentration, the resulting crude material was filtered through a plug of silica gel and rinsed with 50% Et₂O/hexanes. The resulting mixture was concentrated to yield the title compound as a golden oil.

Example 28

2-Allyloxy-2-trifluoromethyl-but-3-enoic acid ethyl ester

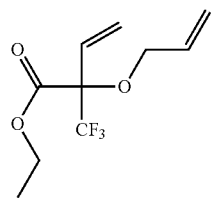 [SMILES: C=CCOC(C=C)(C(=O)OCC)C(F)(F)F]

To a solution of 2-hydroxy-2-trifluoromethyl-but-3-enoic acid ethyl ester (3.6 g) in THF (100 mL) at 0° C. was added sodium hydride (1.1 g of 60% in oil), followed by addition of allyl bromide (2.3 mL) and tetrabutyl ammonium iodide (1.35 g). The resulting mixture was then heated to reflux for 5 h. The reaction was carefully quenched with NH₄Cl (aq), extracted with EtOAc, and dried over Na₂SO₄. After concentration, the resulting crude material was filtered through a plug of silica gel and rinsed with 20% CH₂Cl₂/hexanes, then concentrated to yield the title compound as a yellow oil.

Example 29

2-Trifluoromethyl-2,5-dihydro-furan-2-carboxylic acid ethyl ester

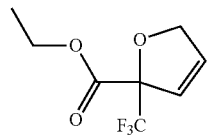

To a solution of 2-allyloxy-2-trifluoromethyl-but-3-enoic acid ethyl ester (2.15 g, see above) in CH$_2$Cl$_2$ (100 mL) at room temperature was added Grubbs catalyst 2$^{nd}$ generation (Aldrich) (67 mg). The resulting mixture was stirred for 18 h at room temperature. The reaction mixture was then filtered through a plug of Celite® and silica gel, rinsed with EtOAc and then concentrated to yield the title compound as a yellow oil.

Example 30

5,6-Dichloro-2-(2-trifluoromethyl-2,5-dihydro-furan-2-yl)-1H-benzoimidazole (#45)

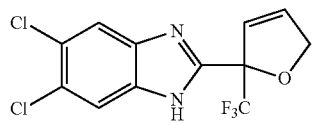 [SMILES: FC(F)(F)C1(c2nc3cc(Cl)c(Cl)cc3[nH]2)C=CCO1]

To 4,5-dichloro-1,2-diamine (1.56 g) in toluene (10 mL) at 0° C. was added neat diethyl aluminum chloride (0.55 mL) and the reaction mixture allowed to warm to room temperature, then stirred for 1 hr. To the resulting purple-colored slurry, at 0° C., was added 2-trifluoromethyl-2,5-dihydro-furan-2-carboxylic acid ethyl ester (464 mg). The resulting mixture was stirred at room temperature for 1 hour, then heated to 110° C. for 20 hours. The reaction mixture was quenched with 6N HCl, diluted with EtOAc, and washed with 6 N HCl. The organic extracts were dried over Na$_2$SO$_4$, filtered, and concentrated to yield a residue. The residue was purified by flash chromatography with Biotage 40s+ column and elution with 10%-40% EtOAc/hexanes to yield an orange gum. The orange gum was dissolved in a minimal amount of CH$_2$Cl$_2$ and triturated with hexanes to yield the title compound as a white powder.

$^1$H NMR (300 MHz, d$_6$-DMSO): δ 13.14 (s, 1H), 7.98 (br, 1H), 7.72 (br, 1H), 6.62 (d, 1H, J=6.2 Hz), 6.26 (d, 1H, J=6.1 Hz), 4.98 (s, 2H)

MS (M+1)=323.0

Example 31

5,6-Dichloro-2-(2-trifluoromethyl-tetrahydro-furan-2-yl)-1H-benzoimidazole (#46)

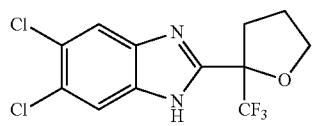 [SMILES: FC(F)(F)C1(c2nc3cc(Cl)c(Cl)cc3[nH]2)CCCO1]

To 5,6-dichloro-2-(2-trifluoromethyl-2,5-dihydro-furan-2-yl)-1H-benzimidazole (95 mg) in methanol (5 mL) was added Rhodium on alumina (32 mg). The resulting mixture was stirred at room temperature under a H$_2$ atmosphere via balloon for 5 hours. The reaction mixture was then filtered through a pad of Celite®, rinsed with Et$_2$O, and concentrated to yield the title compound as a tan solid.

$^1$H NMR (300 MHz, d$_6$-DMSO): δ 13.12 (br, 1H), 7.92 (br, 1H), 7.74 (br, 1H), 4.09-4.14 (m, 2H), 2.75-2.84 (m, 1H), 2.54-2.61 (m, 1H), 2.07-2.13 (m, 1H), 1.89-1.99 (m, 1H)

Example 32

2-(5,6-Dichloro-1H-benzoimidazol-2-yl)-3-ethyl-1,1,1-trifluoro-penta-3,4-dien-2-ol (#62)

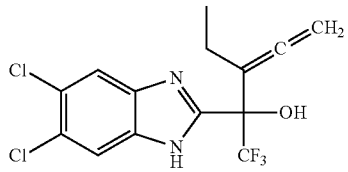 [SMILES: C=C=C(CC)C(O)(c1nc2cc(Cl)c(Cl)cc2[nH]1)C(F)(F)F]

1-(5,6-Dichloro-1H-benzoimidazol-2-yl)-2,2,2-trifluoro-ethanone (2 g), 1-bromo-2-pentyne (1.1 ml) and indium (983 mg) were suspended in THF (15 mL) and H$_2$O (45 mL) and stirred vigorously overnight. The reaction mixture was then diluted with water and ethyl acetate, the layers were separated and the aqueous layer was extracted with ethyl acetate. The combined extracts were washed with brine and dried over Na$_2$SO$_4$ to yield a crude material. The crude material was purified by column chromatography (SiO$_2$; 5-30% ethyl acetate/hexanes) to yield the title compound as a peach-colored solid.

$^1$H NMR (300 MHz, d$_6$-DMSO): δ 12.95 (br, 1H), 7.98 (br, 1H), 7.80 (s, 1H), 7.70 (br, 1H), 5.12 (m, 2H), 1.96-2.09 (m, 1H), 1.66-1.79 (m, 1H)

MS (M+H)=351

Example 33

5,6-Dichloro-2-(2-trifluoromethyl-[1,3]dioxolan-2-yl)-1H-benzimidazole (#47)

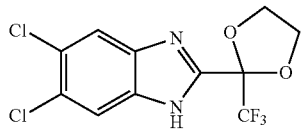 [SMILES: FC(F)(F)C1(c2nc3cc(Cl)c(Cl)cc3[nH]2)OCCO1]

1-(5,6-DiChloro-1H-benzoimidazol-2-yl)-2,2,2-trifluoro-ethanone (1.14 g; 4.02 mmol), 2-chloroethanol (0.83 mL; 12.4 mmol) and potassium carbonate (1.68 g; 12.2 mmol) were dissolved in DMF (18 mL). The reaction mixture was stirred for 18 hrs at ambient temperature, then diluted with ethyl acetate (80 mL), washed with water (50 mL) and brine (2×50 mL). The extracts were dried over Na$_2$SO$_4$, filtered, concentrated to a light brown solid and the light brown solid purified by column chromatography (SiO$_2$; 30% ethyl acetate/hexanes) to yield the title compound as a tan solid.

$^1$H NMR (400 MHz, CD$_3$CN): δ 7.83 (s, 2H), δ 4.29 (m, 4H)

MS calculated for C$_{11}$H$_7$Cl$_2$F$_3$N$_2$O$_2$: 327.09

MS measured: 327, 329 (M+1); 325, 327 (M−H).

Example 34

5,6-Dichloro-2-(2-trifluoromethyl-[1,3]dioxan-2-yl)-1H-benzimidazole (#51)

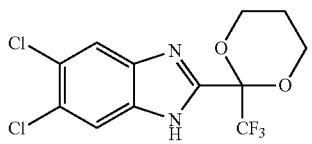 [SMILES: FC(F)(F)C1(c2nc3cc(Cl)c(Cl)cc3[nH]2)OCCCO1]

1-(5,6-DiChloro-1H-benzoimidazol-2-yl)-2,2,2-trifluoroethanone (2.13 g; 7.51 mmol), 2-chloroethanol (1.90 mL; 22.7 mmol) and potassium carbonate (3.13 g; 22.6 mmol) were dissolved in DMF (14 mL). The reaction mixture was stirred for 18 hrs at ambient temperature, then diluted with ethyl acetate (100 mL), washed with water (80 mL) and brine (2×80 mL). The extracts were dried over $Na_2SO_4$, filtered, concentrated to a light brown solid and the light brown solid purified by column chromatography ($SiO_2$; 20% ethyl acetate/hexanes) to yield the title compound as a light yellow solid.

$^1$H NMR (400 MHz, $CD_3CN$): δ 7.84 (s, 2H), δ 4.14 (m, 2H), δ 3.95 (m, 2H), δ 2.16 (m, 2H)

MS calculated for $C_{12}H_9Cl_2F_3N_2O_2$: 341.11

MS measured: 341, 343 (M+1); 339, 341 (M−H).

Example 35

5,6-Dichloro-2-(2-trifluoromethyl-imidazolidin-2-yl)-1H-benzimidazole (#60)

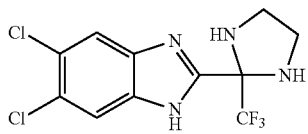 [SMILES: FC(F)(F)C1(c2nc3cc(Cl)c(Cl)cc3[nH]2)NCCN1]

1-(5,6-DiChloro-1H-benzoimidazol-2-yl)-2,2,2-trifluoroethanone (1.02 g; 3.61 mmol), ethylene diamine (0.74 mL; 11.04 mmol) and para-toluenesulphonic acid monohydrate (0.12 g; 0.603 mmol) were suspended in toluene (80 mL), then heated to reflux with a Dean-Stark trap for 3 hrs. After 3 hrs, ethylene diamine (0.74 mL; 11.04 mmol) was added to the reaction mixture and the reaction mixture was allowed to reflux with the Dean-Stark trap for 18 hrs. The reaction was cooled to room temperature and concentrated in vacuo to a crude brown residue. The crude brown residue was dissolved in ethyl acetate (60 mL), washed with water (3×50 mL) and brine (50 mL), then dried over $Na_2SO_4$. The drying agent was removed by filtration and the filtrate was concentrated in vacuo to a crude brown oil, which was purified by column chromatography ($SiO_2$, 50% ethyl acetate/hexanes) to yield the title compound as a light orange solid.

$^1$H NMR (400 MHz, $CD_3CN$): δ 7.80 (s, 2H), δ 3.32 (br s, 2H), δ 3.06 (m, 2H)

MS calculated for $C_{11}H_9Cl_2F_3N_4$: 325.12

MS measured: 325, 327 (M+1), 323, 325 (M−H).

Example 36

5,6-Dichloro-1-pyridin-2-ylmethyl-2-(2-trifluoromethyl-[1,3]dioxin-2-yl)-1H-benzimidazole (#48)

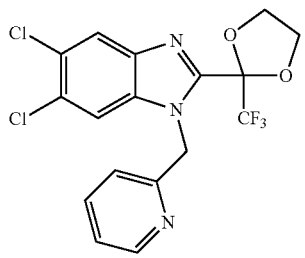 [SMILES: FC(F)(F)C1(c2nc3cc(Cl)c(Cl)cc3n2Cc2ccccn2)OCCO1]

5,6-Dichloro-2-(2-trifluoromethyl-[1,3]dioxolan-2-yl)-1H-benzimidazole (0.37 g; 1.1 mmol) was dissolved in DMF (6 mL), treated with 60% NaH in mineral oil 9.14 g; 3.5 mmol) and stirred under a nitrogen atmosphere for 20 minutes. Subsequently, 2-(Bromomethyl)pyridine hydrobromide (0.44 g; 1.7 mmol) was added to the reaction mixture and stirred at room temperature overnight. The reaction mixture was diluted with ethyl acetate (25 mL) and diethyl ether (25 mL), washed with water (30 mL) and brine (3×30 mL), then dried over $Na_2SO_4$. The concentrated crude material was purified by column chromatography ($SiO_2$; 50% ethyl acetate/hexanes) to yield the title compound as an off-white solid.

$^1$H NMR (400 MHz, $CD_3CN$): δ 8.42 (d, J=4.5 Hz, 1H), δ 7.96 (s, 1H), δ 7.70 (d, J=1.6 Hz, 1H), δ 7.67 (s, 1H), δ 7.24 (m, 1H), δ 7.05 (d, J=7.9 Hz, 1H), δ5.67 (s, 2H), δ 4.19 (t, J=7.0 Hz, 2H), δ 3.95 (m, 2H)

MS calculated for $C_{17}H_{12}Cl_2F_3N_3O_2$: 418.20

MS measured: 418, 420 (M+H).

Example 37

6-Trifluoromethyl-2-(2-trifluoromethyl-[1,3]-dioxolan-2-yl)-1H-benzimidazole-5-carbonitrile (#59)

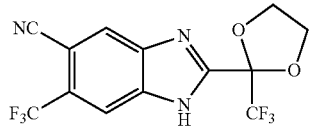

2-(2,2,2-Trifluoro-acetyl)-6-trifluoromethyl-1H-benzoimidazole-5-carbonitrile (0.50 g; 1.5 mmol), was dissolved in DMF (4 mL), then treated with 2-chloroethanol (0.35 mL; 5.2 mmol) and potassium carbonate (0.73 g; 5.3 mmol). The reaction mixture was stirred at room temperature overnight. The reaction mixture was then diluted with ethyl acetate (40 mL) and diethyl ether (40 mL), washed with water (50 mL) and brine (3×30 mL), then dried over $Na_2SO_4$. The reaction mixture was filtered, concentrated to yield a light brown solid, which was purified by column chromatography ($SiO_2$; 100% ethyl acetate) to yield the title compound as a light yellow solid.

$^1$H NMR (400 MHz, $CD_3CN$): δ 8.31 (s, 1H), δ 8.17 (s, 1H), δ 4.36 (m, 2H), δ 4.30 (m, 1H)

MS calculated for $C_{13}H_7F_6N_3O_2$: 351.20
MS measured: 352 (M+1), 350 (M–H).

Example 38

General Procedure for the Alkylation of 5,6-Dichloro-2-(2-trifluoromethyl-[1,3]-dioxolan-2-yl)-1H-benzimidazole To a suspension of NaH (1.25 mmol) in dry DMF (5 mL) was added a solution of 5,6-dichloro-2-(2-trifluoromethyl-[1,3]dioxolan-2-yl)-1H-benzimidazole (1.0 mmol) in dry DMF (5 mL). After stirring the reaction mixture at room temperature for 30 min, the suitably substituted electrophile (1-10 eq) was added dropwise via syringe. The reaction mixture was stirred overnight at room temperature and then poured onto water (125 mL) with rapid stirring. The resulting precipitate was collected by filtration and purified by flash chromatography ($SiO_2$, dcm) to yield the product.

Following the general procedure described above, the following compounds of the present invention were prepared. After each compound name and structure is listed the suitably substituted electrophile used in the reaction.

Example 39

5,6-Dichloro-1-methyl-2-(2-trifluoromethyl-[1,3]-dioxolan-2-yl)-1H-benzoimidazole (#52)

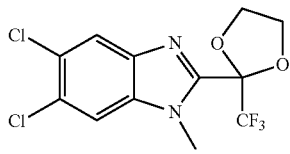 [SMILES: Cn1c(C2(C(F)(F)F)OCCO2)nc2cc(Cl)c(Cl)cc21]

Electrophile: Methyl Iodide
Ms (m/z): 341 (MH+)

Example 40

1-[2-(tert-Butyl-dimethyl-silanyloxy)-ethyl]-5,6-dichloro-2-(2-trifluoromethyl-[1,3]-dioxolan-2-yl)-1H-benzoimidazole (#58)

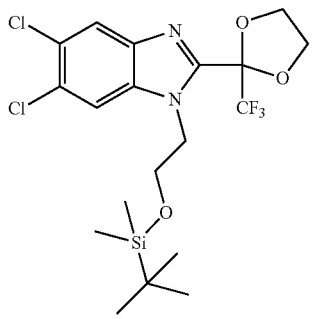 [SMILES: CC(C)(C)[Si](C)(C)OCCn1c(C2(C(F)(F)F)OCCO2)nc2cc(Cl)c(Cl)cc21]

Electrophile: (2-Bromo-ethoxy)-tert-butyl-dimethyl-silane.
Ms (m/z): 485 (MH+)

Example 41

[5,6-Dichloro-2-(2-trifluoromethyl-[1,3]-dioxolan-2-yl)-benzoimidazol-1-yl]-acetonitrile (#53)

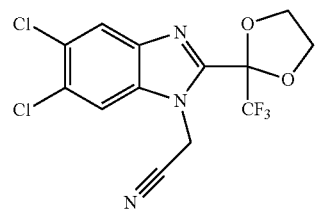 [SMILES: N#CCn1c(C2(C(F)(F)F)OCCO2)nc2cc(Cl)c(Cl)cc21]

Electrophile: Bromoacetonitrile
Ms (m/z): 366 (MH+)

Example 42

[5,6-Dichloro-2-(2-trifluoromethyl-[1,3]-dioxolan-2-yl)-benzoimidazol-1-yl]-acetic acid methyl ester (#57)

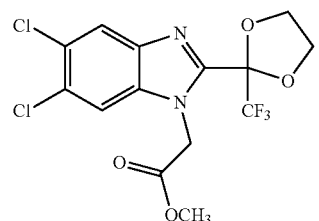

Electrophile: Methyl Iodoacetate
Ms (m/z): 399 (MH+)

Example 43

5,6-Dichloro-1-ethyl-2-(2-trifluoromethyl-[1,3]-dioxolan-2-yl)-1H-benzoimidazole (#56)

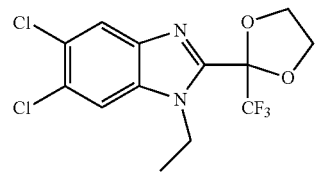 [SMILES: CCn1c(C2(C(F)(F)F)OCCO2)nc2cc(Cl)c(Cl)cc21]

Electrophile: Ethyl Iodide
Ms (m/z): 355 (MH+)

Example 44

1-Allyl-5,6-dichloro-2-(2-trifluoromethyl-[1,3]-dioxolan-2-yl)-1H-benzoimidazole (#55)

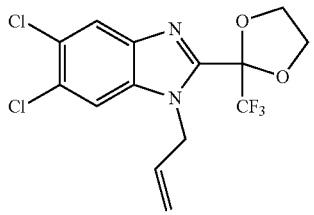 [SMILES: C=CCn1c(C2(C(F)(F)F)OCCO2)nc2cc(Cl)c(Cl)cc21]

Electrophile: Allyl Bromide
Ms (m/z): 367 (MH+)

Example 45

5,6-Dichloro-1-prop-2-ynyl-2-(2-trifluoromethyl-[1,3]-dioxolan-2-yl)-1H-benzoimidazole (#54)

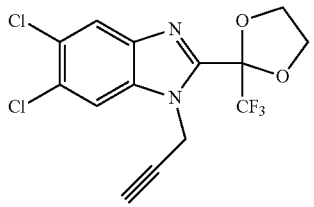 [SMILES: C#CCn1c(C2(C(F)(F)F)OCCO2)nc2cc(Cl)c(Cl)cc21]

Electrophile: Propargyl Bromide
Ms (m/z): 365 (MH+)

Example 46

5,6-Dichloro-2-(2-trifluoromethyl-oxazolidin-2-yl)-1H-benzimidazole (#61)

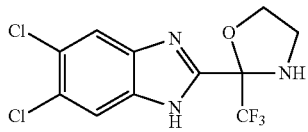 [SMILES: FC(F)(F)C1(c2nc3cc(Cl)c(Cl)cc3[nH]2)NCCO1]

1-(5,6-DiChloro-1H-benzoimidazol-2-yl)-2,2,2-trifluoroethanone (594 mg), 2-bromoethylamine-hydrobromide (860 mg) and potassium carbonate (871 mg) were dissolved in DMF (5 mL). The reaction mixture was stirred for 18 hrs at ambient temperature, then diluted with ethyl acetate (50 mL), washed with water (50 mL) and brine (2×20 mL). The extracts were dried over $Na_2SO_4$, filtered, concentrated, and purified by column chromatography ($SiO_2$; 40% ethyl acetate/hexanes) to yield the title compound as a yellow solid.

$^1$H NMR (400 MHz, $d_6$DMSO): δ 13.19 (s, 1H), 8.01 (br, 1H), 7.72 (br, 1H), 8.01 (br, 1H), 4.50-4.54 (m, 1H), 4.17-4.21 (m, 1H), 3.75-3.81 (m, 1H), 3.39-3.41 (m, 1H), 3.03-3.08 (m, 1H)

MS calculated for $C_{11}H_8Cl_2F_3N_3O$: 325.00, measured as: 326 (M+1).

Example 47

[2-(5,6-Dichloro-1H-benzoimidazol-2-yl)-2-trifluoromethyl-[1,3]-dioxolan-4-yl]-methanol (#49)

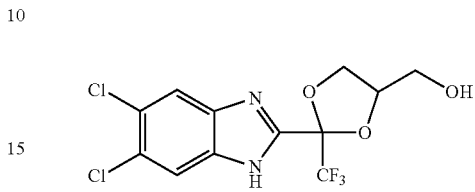

1-(5,6-DiChloro-1H-benzoimidazol-2-yl)-2,2,2-trifluoroethanone (503 mg), 3-chloro-1,2-propan-diol (393 mg) and potassium carbonate (491 mg) were dissolved in DMF (5 mL). The reaction mixture was stirred for 18 hrs at ambient temperature, then diluted with ethyl acetate (50 mL), washed with water (50 mL) and brine (2×20 mL). The extracts were dried over $Na_2SO_4$, filtered, concentrated, and purified by column chromatography ($SiO_2$; 40% ethyl acetate/hexanes), followed by washing solid with $CH_2Cl_2$/hexanes to yield the title compound as an off-white solid.

$^1$H NMR (300 MHz, $d_6$DMSO): δ 13.06 (br, 1H), 7.92 (br, 2H), 5.13 (br, 1H), 4.59-4.66 (m, 1H), 4.46 (apparent t, 1H, J=7.7 Hz), 4.10 (apparent t, 1H, J=7.3 Hz), 3.52-3.63 (m, 2H)

MS calculated for $C_{12}H_9Cl_2F_3N_2O_3$: 355.99
Measured: 357 (M+1).

Example 48

5,6-Dichloro-2-(4-chloromethyl-2-trifluoromethyl-[1,3]-dioxolan-2-yl)-1H-benzimidazole (#50)

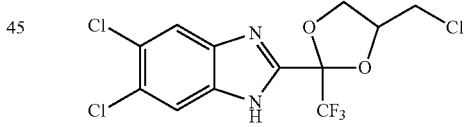

1-(5,6-Dichloro-1H-benzimidazol-2-yl)-2,2,2-trifluoroethanone (611 mg), 1,3-dichloro-2-propanl (557 mg) and potassium carbonate (597 mg) were dissolved in DMF (5 mL). The reaction mixture was stirred for 18 hrs at ambient temperature, then diluted with ethyl acetate (50 mL), washed with water (50 mL) and brine (2×20 mL). The extracts were dried over $Na_2SO_4$, filtered, concentrated and purified by column chromatography ($SiO_2$; 40% ethyl acetat/hexanes), followed by washing the solid with $CH_2Cl_2$/hexanes to yield the title compound as an off-white solid.

$^1$H NMR (300 MHz, $d_6$DMSO): δ 13.40 (br, 1H0, 8.05 (br, 1H), 4.72-4.78 (m, 1H), 4.41-4.46 (m, 1H), 4.09-4.14 (m, 1H), 3.97 (dd, 1H, J=11.8, 4.4 Hz), 3.86 (dd, 1H, J=11.0, 6.2 Hz)

MS Calculated for $C_{12}H_8Cl_3F_3N_2)_2$: 373.96
Measured as 375 (M+1)

Example 49

2-(5,6-Dichloro-1-methyl-1H-benzoimidazol-2-yl)-1,1,1-trifluoro-pent-4-yn-2-ol #35

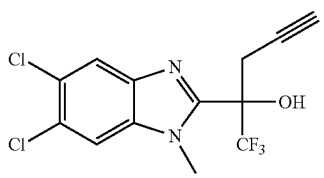 [SMILES: C#CCC(O)(c1nc2cc(Cl)c(Cl)cc2n1C)C(F)(F)F]

To a solution of Compound #2 prepared as in Example 4 above, (323 mg, 1 mmol) in dry DMF was added sodium hydride (60 mg, 1.5 mmol, 60% in mineral oil). The resulting mixture was then stirred at room temperature for 30 mins, cooled to 0° C. and treated with iodomethane (63 μL, 1 mmol). After stirring for four hours, TLC indicated consumption of starting material. Water was added and the product extracted into ethyl acetate. The organic layer was washed with 15% LiCl and then brine. After drying (MgSO$_4$), the solvent was removed in vacuo to yield the title compound as a solid.

MS (m/z): 338 (M+H)

(+)-Enantiomer of 2-(5,6-Dichloro-1-methyl-1H-benzoimidazol-2-yl)-1,1,1-trifluoro-pent-4-yn-2-ol (#36) and (−)-Enantiomer of 2-(5,6-Dichloro-1-methyl-1H-benzoimidazol-2-yl)-1,1,1-trifluoro-pent-4-yn-2-ol (#37)

Compounds #36 was similarly prepared according to the procedure described above, starting with the (+)-enantiomer, Compound #31, prepared as in Example 4 above.

Compounds #37 was similarly prepared according to the procedure described in Example 49 above, starting from (−)-enantiomer, Compound #32, prepared as in Example 4 above.

Example 50

Ventral Prostate and Levator Ani Weight In Vivo Assay

Immature Rats

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle) and with testosterone propionate (given subcutaneously by injection at the nape of the neck at 2 mg/kg, in a volume of 0.1 mL in sesame oil). On the sixth day, the rats were euthanized by asphyxiation in carbon dioxide. Ventral prostates and levator ani were removed and their wet weights determined. Test compound activity was determined as the percent inhibition of testosterone-enhanced tissue weights, with a vehicle-treated control group set to zero percent and a testosterone alone-treated control group set to 100%.

Mature Rats

Mature (150- to 200-g) castrated male Sprague Dawley rats (Charles River) are similarly tested according to the procedure described above. The rats were dosed for two weeks, with 0.4 mg/kg testosterone propionate used as the positive control.

Representative compounds of the present invention were tested according to the procedure described above, with results as listed in Table 3 below. For effect on prostate—i.e. an antagonist—a test compound is listed as "active" in the Table below if the non weight adjusted prostate weight was ≤40 mg or the % Inhibition prostate weight, body weight adjusted was ≥40% @ 2 mg/day dosage. For effect on levator ani—i.e. an agonist—a test compound is listed as "active" in the Table below if the non weight adjusted levator ani weight was ≥40 mg or the % Stimulation levator ani weight, body weight adjusted was ≥40% at 2 mg/day dosage.

Note that while certain of the compounds listed in Table 3 may or may not have shown an effect on prostate and/or levator ani weight, they are listed herein as "inactive" as they did not meet the specified criteria defined above.

TABLE 3

| ID No. | Prostate antagonist | L.A. agonist |
| --- | --- | --- |
| 1 | active | inactive |
| 2 | active | active |
| 3 | active | active |
| 4 | active | active |
| 6 | active | inactive |
| 7 | inactive | active |
| 8 | active | inactive |
| 9 | active | inactive |
| 10 | active | inactive |
| 13 | active | inactive |
| 14 | active | inactive |
| 15 | active | active |
| 16 | active | inactive |
| 17 | active | inactive |
| 23 | active | inactive |
| 24 | active | inactive |
| 25 | active | inactive |
| 26 | active | inactive |
| 27 | inactive | inactive |
| 28 | active | inactive |
| 31 | active | active |
| 32 | active | inactive |
| 34 | inactive | inactive |
| 35 | inactive | |
| 36 | inactive | inactive |
| 37 | inactive | active |
| 38 | active | active |
| 39 | active | inactive |
| 40 | active | |
| 41 | active | inactive |
| 42 | active | inactive |
| 43 | inactive | active |
| 44 | inactive | inactive |
| 45 | inactive | active |
| 46 | active | active |
| 47 | active | |
| 48 | inactive | inactive |
| 49 | active | inactive |
| 50 | active | |
| 51 | active | inactive |
| 52 | inactive | |
| 53 | active | |
| 54 | active | |
| 55 | active | |
| 56 | active | |
| 57 | inactive | |
| 59 | active | inactive |
| 60 | active | |
| 61 | active | inactive |
| 62 | active | |

Example 51

As a specific embodiment of an oral composition, 50 mg of Compound #43 prepared as described in Example 26 above is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A method of treating
a condition selected from the group consisting of prostate carcinoma, benign prostatic hyperplasia (BPH), hirsutism, alopecia, anorexia nervosa, breast cancer, acne, cachexia, diminished libido, male contraception, and male performance,
comprising administering to a subject in need thereof a therapeutically effective amount of a compound of formula (I)

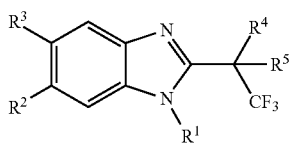

wherein
$R^1$ is selected from the group consisting of hydrogen or lower alkyl,
$R^2$ and $R^3$ are halogen;
$R^4$ is alkenyl or alkynyl,
wherein the alkenyl or alkynyl is optionally substituted with one or more substituents independently selected from the group consisting of halogen, hydroxy, carboxy, cyano, nitro, $NR^ER^F$, $NR^E$—C(O)-lower alkyl and phenyl; wherein $R^E$ and $R^F$ are each independently selected from hydrogen or lower alkyl; and wherein the phenyl is optionally substituted with one to four substituents independently selected from the group consisting of halogen, lower alkyl, lower alkoxy, hydroxy, carboxy, cyano, nitro, amino, (lower alkyl)amino and di(lower alkyl)amino;
$R^5$ is OH;
alternatively, $R^4$ and $R^5$ are taken together with the atom to which they are bound to form a ring structure selected from the group consisting of 2-pyrrolidinyl, 2-tetrahydro-furanyl, 2-(2,5-dihydro-1H-pyrrolyl), 2-(2,5-dihydro-furanyl), 2-imidazolidinyl, 2-oxazolidinyl, 2-[1,3]-dioxolanyl, 2-piperidinyl, 6-(1,2,3,6-tetrahydro-pyridinyl), 2-(1,2,3,6-tetrahydro-pyridinyl), 2-tetrahydropyranyl, 6-(3,6-dihydro-2H-pyranyl), 2-(3,6-dihydro-2H-pyranyl), 2-(hexahydro-pyrimidinyl), 2-[1,3]oxazinanyl, 2-imidazolyl, and 2-[1,3]dioxanyl;
wherein the ring structure is optionally substituted with one or more substituents independently selected from the group consisting of lower alkyl, -(lower alkyl)-OH and -(lower alkyl)-(halogen);
and pharmaceutically acceptable salts thereof.

2. The method of claim 1 comprising treating the subject with a pharmaceutical composition comprising a pharmaceutically acceptable carrier and the compound of formula (I).

3. The method of claim 1 in which, in the compound of formula (I),
$R^2$ and $R^3$ are each independently halogen;
$R^4$ is alkenyl or alkynyl; wherein the alkenyl is optionally substituted with a substituent selected from the group consisting of hydroxy, carboxy and phenyl;
$R^5$ is OH;
alternatively, $R^4$ and $R^5$ are taken together with the atom to which they are bound to form a ring structure selected from the group consisting of 2-(2,5-dihydro-furanyl), 2-tetrahydrofuranyl, 2-[1,3]-dioxolanyl, 2-[1,3]dioxanyl, 2-imidazolyl and 2-oxazolidinyl;
wherein the ring structure is optionally substituted with one to two substituents independently selected from the group consisting of methyl, ethyl, hydroxymethyl, hydroxyethyl, and —($C_{1-2}$alkyl)-halogen;
or a pharmaceutically acceptable salt thereof.

4. The method of claim 1 in which, in the compound of formula (I),
$R^1$ is selected from the group consisting of hydrogen, methyl, and ethyl;
$R^2$ is chloro;
$R^3$ is chloro;
$R^4$ is selected from the group consisting of vinyl, (+)-vinyl, (−)-vinyl, allyl, (+)-allyl, (−)-allyl, 2-methyl-allyl, 2-propen-3-yl, Z-2-propen-3-yl, E-2-propen-3-yl, 3-methyl-1-propen-3-yl, 2-carboxy-1-propen-3-yl, 3-phenyl-1-propen-3-yl, 3,3-dimethyl-1-propen-3-yl, 2,3-dimethyl-2-propen-3-yl, 2-methyl-2-propen-3-yl, isopropenyl, propa-1,2-dien-3-yl, 3-methyl-propa-1,2-dien-3-yl, 3-ethyl-propa-1,2-dien-3-yl), 1-buten-4-yl, 1-propyn-3-yl, (+)-1-propyn-3-yl, (−)-1-propyn-3-yl, 2-propyn-3-yl, 1-hydroxy-2-propyn-3-yl, 1-phenyl-1-propyn-3-yl, and 2-butyn-4-yl;
$R^5$ is OH;
alternatively, $R^4$ and $R^5$ are taken together with the atom to which they are bound to form a ring structure selected from the group consisting of 2-(2,5-dihydro-furanyl), 2-tetrahydrofuranyl, 2-[1,3]-dioxolanyl, 2-(4-hydroxymethyl-[1,3]dioxalanyl), 2-(4-chloromethyl-[1,3]dioxolanyl, 2-[1,3]dioxanyl, 2-imidazolyl and 2-oxazolidinyl;
or a pharmaceutically acceptable salt thereof.

5. The method of claim 1 in which, in the compound of formula (I),
$R^1$ is selected from the group consisting of hydrogen and ethyl;
$R^4$ is selected from the group consisting of vinyl, allyl, (+)-allyl, (−)-allyl, 2-methyl-allyl, 2-propen-3-yl, Z-2-propen-3-yl, E-2-propen-3-yl, 3-methyl-1-propen-3-yl, 3-phenyl-1-propen-3-yl, 3,3-dimethyl-1-propen-3-yl, 2,3-dimethyl-2-propen-3-yl, 2-methyl-2-propen-3-yl, isopropenyl, propa-1,2-dien-3-yl, 3-methyl-propa-1,2-dien-3-yl, 3-ethyl-propa-1,2-dien-3-yl, 1-buten-4-yl, 1-propyn-3-yl, (+)-1-propyn-3-yl, (−)-1-propyn-3-yl, and 2-propyn-3-yl;
$R^5$ is OH;
alternatively, $R^4$ and $R^5$ are taken together with the atom to which they are bound to form a ring structure selected from the group consisting of 2-tetrahydrofuranyl, 2-[1,3]-dioxolanyl, 2-(4-hydroxymethyl-[1,3]dioxolanyl), 2-(4-chloromethyl-[1,3]dioxolanyl, 2-[1,3]dioxanyl, 2-imidazolyl and 2-oxazolidinyl;
or a pharmaceutically acceptable salt thereof.

6. The method of claim 1 in which, in the compound of formula (I),
$R^1$ is selected from the group consisting of hydrogen and methyl;
$R^4$ is selected from the group consisting of vinyl, (+)-vinyl, allyl, Z-2-propen-3-yl, propa-1,2-dien-3-yl, 1-propyn-3-yl, (+)-1-propyn-3-yl and (−)-1-propyn-3-yl;
$R^5$ is OH;

alternatively, $R^4$ and $R^5$ are taken together with the atom to which they are bound to form a ring structure selected from the group consisting of 2-(2,5-dihydro-furanyl), and 2-tetrahydrofuranyl;

or a pharmaceutically acceptable salt thereof.

7. The method of claim 1 in which, in the compound of formula (I), $R^1$ is hydrogen;

$R^4$ is selected from the group consisting of isopropenyl, Z-2-propen-3-yl and (+)-vinyl;

$R^5$ is OH;

alternatively, $R^4$ and $R^5$ are taken together with the atom to which they are bound to form 2-[1,3]dioxolanyl;

or a pharmaceutically acceptable salt thereof.

8. The method of claim 1 in which, in the compound of formula (I), $R^1$ is selected from the group consisting of hydrogen and lower alkyl;

$R^2$ and $R^3$ are each halogen;

$R^4$ is alkenyl or alkynyl; wherein the alkenyl is optionally substituted with a substituent selected from the group consisting of hydroxy, carboxy and phenyl;

$R^5$ is OH;

or a pharmaceutically acceptable salt thereof.

9. The method of claim 1 in which, in the compound of formula (I), $R^1$ is selected from the group consisting of hydrogen and methyl;

$R^4$ is selected from the group consisting of vinyl, (+)-vinyl, (−)-vinyl, allyl, (+)-allyl, (−)-allyl, 2-methyl-allyl, 2-propen-3-yl, Z-2-propen-3-yl, E-2-propen-3-yl, 3-methyl-1-propen-3-yl, 2-carboxy-1-propen-3-yl, 3-phenyl-1-propen-3-yl, 3,3-dimethyl-1-propen-3-yl, 2,3-dimethyl-2-propen-3-yl, 2-methyl-2-propen-3-yl), isopropenyl, propa-1,2-dien-3-yl, 3-methyl-propa-1,2-dien-3-yl, 3-ethyl-propa-1,2-dien-3-yl, 1-buten-4-yl, 1-propyn-3-yl, 2-propyn-3-yl, (+)-1-propyn-3-yl, (−)-1-propyn-3-yl, 1-hydroxy-2-propyn-3-yl, 1-phenyl-1-propyn-3-yl, and 2-butyn-4-yl;

$R^5$ is OH;

or a pharmaceutically acceptable salt thereof.

10. The method of claim 1 in which, in the compound of formula (I), $R^1$ is hydrogen;

$R^2$ and $R^3$ are each chloro;

$R^4$ is selected from the group consisting of isopropenyl, Z-2-propen-3-yl and (+)-vinyl;

$R^5$ is OH;

or a pharmaceutically acceptable salt thereof.

11. The method of claim 1 in which, in the compound of formula (I), $R^2$ and $R^3$ are each independently halogen;

$R^4$ and $R^5$ are taken together with the atom to which they are bound to form a ring structure selected from the group consisting of 2-(2,5-dihydro-furanyl), 2-tetrahydrofuranyl, 2-[1,3]-dioxolanyl, 2-[1,3]dioxanyl, 2-imidazolyl and 2-oxazolidinyl;

wherein the ring structure is optionally substituted with one to two substituents independently selected from the group consisting of hydroxymethyl, hydroxyethyl, and —($C_{1-2}$alkyl)-halogen;

or a pharmaceutically acceptable salt thereof.

12. The method of claim 1 in which, in the compound of formula (I), $R^1$ is selected from the group consisting of hydrogen, methyl, and ethyl;

$R^2$ is selected from the group consisting of chloro;

$R^3$ is chloro;

$R^4$ and $R^5$ are taken together with the atom to which they are bound to form a ring structure selected from the group consisting of 2-(2,5-dihydro-furanyl), 2-tetrahydrofuranyl, 2-[1,3]-dioxolanyl, 2-(4-hydroxymethyl-[1,3]dioxalanyl), 2-(4-chloromethyl-[1,3]dioxolanyl, 2-[1,3]dioxanyl, 2-imidazolyl and 2-oxazolidinyl;

or a pharmaceutically acceptable salt thereof.

13. The method of claim 1 in which, in the compound of formula (I), $R^1$ is hydrogen;

$R^2$ and $R^3$ are each chloro;

$R^4$ and $R^5$ are taken together with the atom to which they are bound to form 2-[1,3]dioxolanyl;

or a pharmaceutically acceptable salt thereof.

* * * * *